US011744862B2

(12) United States Patent
Wang et al.

(10) Patent No.: US 11,744,862 B2
(45) Date of Patent: Sep. 5, 2023

(54) CS1 TARGETED CHIMERIC ANTIGEN RECEPTOR-MODIFIED T CELLS FOR TREATMENT OF AL AMYLOIDOSIS

(71) Applicant: City of Hope, Duarte, CA (US)

(72) Inventors: Xiuli Wang, Temple City, CA (US); Stephen J. Forman, Duarte, CA (US)

(73) Assignee: City of Hope, Duarte, CA (US)

( * ) Notice: Subject to any disclaimer, the term of this patent is extended or adjusted under 35 U.S.C. 154(b) by 799 days.

(21) Appl. No.: 16/496,271

(22) PCT Filed: Mar. 20, 2018

(86) PCT No.: PCT/US2018/023381
§ 371 (c)(1),
(2) Date: Sep. 20, 2019

(87) PCT Pub. No.: WO2018/175453
PCT Pub. Date: Sep. 27, 2018

(65) Prior Publication Data
US 2020/0188432 A1 Jun. 18, 2020

Related U.S. Application Data

(60) Provisional application No. 62/473,980, filed on Mar. 20, 2017.

(51) Int. Cl.
| | |
|---|---|
| *A61K 35/17* | (2015.01) |
| *C07K 14/725* | (2006.01) |
| *C07K 14/73* | (2006.01) |
| *C07K 14/705* | (2006.01) |
| *C07K 16/28* | (2006.01) |
| *C12N 5/0783* | (2010.01) |
| *C12N 15/86* | (2006.01) |
| *A61K 38/00* | (2006.01) |

(52) U.S. Cl.
CPC .......... *A61K 35/17* (2013.01); *C07K 14/7051* (2013.01); *C07K 14/70514* (2013.01); *C07K 14/70521* (2013.01); *C07K 14/70578* (2013.01); *C07K 16/2803* (2013.01); *C12N 5/0636* (2013.01); *C12N 15/86* (2013.01); *A61K 38/00* (2013.01); *C07K 2317/622* (2013.01); *C07K 2319/03* (2013.01); *C07K 2319/33* (2013.01); *C12N 2510/00* (2013.01); *C12N 2740/15043* (2013.01)

(58) Field of Classification Search
CPC ......... A61K 35/14; C07K 16/28; C07K 16/46
See application file for complete search history.

(56) References Cited

FOREIGN PATENT DOCUMENTS

| AU | 2013205096 | 5/2013 | | |
|---|---|---|---|---|
| ES | 2365337 | * 11/2011 | ........... | A61K 39/395 |
| RU | 2475500 | 2/2013 | | |
| WO | WO2014179759 | * 11/2014 | ............ | C07K 19/00 |
| WO | WO 2016/090369 | 6/2016 | | |

OTHER PUBLICATIONS

Brown et al., "Regression of Glioblastoma after Chimeric Antigen Receptor T-Cell Therapy," N Engl J Med., Dec. 29, 2016, 375(26):2561-2569.
Chu et al., "CS1-specific chimeric antigen receptor (CAR)-engineered natural killer cells enhance in vitro and in vivo antitumor activity against human multiple myeloma," Leukemia, Sep. 26, 2013, 28(4):917-927.
Falk et al., "The Systemic Amyloidoses," N Engl J Med., 1997, 337:898-909.
Fesnak et al., "Engineered T cells: the promise and challenges of cancer immunotherapy," Nature Reviews Cancer, Aug. 23, 2016, 16(9):566-581.
International Preliminary Report on Patentability in International Application No. PCT/US2018/023381, dated Sep. 24, 2019, 8 pages.
International Search Report and Written Opinion in International Application No. PCT/US2018/023381, dated Jul. 30, 2018, 17 pages.
Kyle et al., "A trial of three regimens for primary amyloidosis: colchicine alone, melphalan and prednisone, and melphalan, prednisone, and colchicine," N Engl J Med., 1997, 336(17):1202-1207.
Lee et al., "Evaluation of B cell maturation antigen as a target for antibody drug conjugate mediated cytotoxicity in multiple myeloma," British J of Haematology, Jun. 17, 2016, 174(6):911-922.
Lonial et al., "Elotuzumab Therapy for Relapsed or Refractory Multiple Myeloma," N Engl J Med., Aug. 13, 2015, 373(7):621-631.
Nuvolone et al., "Systemic amyloidosis: novel therapies and role of biomarkers," Nephrol Dial Transplant., Aug. 18, 2016, 32(5):770-780.
Rosenzweig et al., "Preclinical data support leveraging CS1 chimeric antigen receptor T-cell therapy for systemic light chain amyloidosis," Cytotherapy, May 5, 2017, 19(7):861-866.
Suzuki, "Diagnosis and treatment of multiple myeloma and AL amyloidosis with focus on improvement of renal lesion," Clinical and Experimental Nephrology, Sep. 13, 2012, 16(5):659-671.
Wang et al., "A transgene-encoded cell surface polypeptide for selection, in vivo tracking, and ablation of engineered cells," Aug. 4, 2011, Blood, 118(5):1255-1263.
Wang et al., "Phenotypic and functional attributes of lentivirus-modified CD19-specific human CD8+ central memory T cells manufactured at clinical scale," J Immunology., 2012, 35(9):689-701.
Fujiwara et al., "Hinge and Transmembrane Domains of Chimeric Antigen Receptor Regulate Receptor Expression and Signaling Threshold," Cells, May 2020, 9(5):1182.

(Continued)

*Primary Examiner* — Elly-Gerald Stoica
(74) *Attorney, Agent, or Firm* — Fish & Richardson P.C.

(57) ABSTRACT

Methods for treating AL amyloidosis using chimeric antigen receptors targeting CS1 are described.

11 Claims, 9 Drawing Sheets

Specification includes a Sequence Listing.

(56) References Cited

OTHER PUBLICATIONS

Fujiwara et al. "Impact of scFv structure in chimeric antigen receptor on receptor expression efficiency and antigen recognition properties," Biochemical and Biophysical Research Communications, 2020, 527:350-357.

Lisenko et al., "Flow cytometry-based characterization of underlying clonal B and plasma cells in patients with light chain amyloidosis," Cancer Med., Jul. 2016, 5(7):1464-1472.

Zhong et al., "Chimeric antigen receptors combining 4-1BB and CD28 signaling domains augment PI3kinase/AKT/Bcl-XL activation and CD8+ T cell-mediated tumor eradication," Molecular therapy: the journal of the American Society of Gene Therapy, 2010, 18(2):413-420.

Zhao et al., "Structural Design of Engineered Costimulation Determines Tumor Rejection Kinetics and Persistence of CAR T Cells," Cancer cell, 2015, 28(4):415-428.

Desport et al., "AL-Amyloidosis," Нефрология., 2014, 18(4):36-50 (English Abstract Only).

Charlinski Grzegorz et al., "Amyloidosis and other plasmocytic dyscrasias: diagnosis and treatment, Szpiczak Mnogi wybrane zagadnienia," Jan. 2013, pp. 45-67, abstract only.

KR Office Action in Korean Appln No. 10-2019-7030388, dated May 22, 2023, 10 pages (with English translation).

JP Office Action in Japanese Appln. No. 2019-551687, dated Jun. 27, 2023, 8 pages (with English translation).

Schonland et al., "Detection and Characterization of Plasma Cell and B Cell Clones in Patients with Systemic Light Chain Amyloidosis Using FLow Cytometry," Blood, Dec. 6, 2014, 124(21):2068 (4 pages—Abstract).

* cited by examiner

FIGURE 4

MLLLVTSLLLCELPHPAFLLIPEVQLVESGGGLVQPGGSLRLSCAASGFDFSRYWMSWVRQA
GMCSFRa signal peptide (22 aa)    CS1scFv ( aa)

PGKGLEWIGEINPDSSTINYAPSLKDKFIISRDNAKNSLYLQMNSLRAEDTAVYYCARPDGNY

WYFDVWGQGTLVTVSSGSTSGGGSGGGSGGGGSSDIQMTQSPSSLSASVGDRVTITCKAS

QDVGIAVAWYQQKPGKVPKLLIYWASTRHTGVPDRFSGSGSGTDFTLTISSLQPEDVATYYC

QQYSSYPYTFGQGTKVEIKESKYGPPCPPCPGGGSSGGGSGGQPREPQVYTLPPSQEEMTK
                                IgG4-Hinge (12 aa)   Linker (10 aa)    IgG4-CH3

NQVSLTCLVKGFYPSDIAVEWESNGQPENNYKTTPPVLDSDGSFFLYSRLTVDKSRWQEGN

VFSCSVMHEALHNHYTQKSLSLSLGKMFWVLVVVGGVLACYSLLVTVAFIIFWVRSKRSRGG
                                CD28 transmembrane (28 aa)              CD28 (41 aa)

HSDYMNMTPRRPGPTRKHYQPYAPPRDFAAYRSGGGRVKFSRSADAPAYQQGQNQLYNE
                                            Gly3   CD3 Zeta ( 112 aa)

LNLGRREEYDVLDKRRGRDPEMGGKPRRKNPQEGLYNELQKDKMAEAYSEIGMKGERRRG

KGHDGLYQGLSTATKDTYDALHMQALPPRLEGGGEGRGSLLTCGDVEENPGPRMLLLVTSL
                                            T2A (24 aa)                    EGFRt
LLCELPHPAFLLIPRKVCNGIGIGEFKDSLSINATNIKHFKNCTSISGDLHILPVAFRGDSFTHTP

PLDPQELDILKTVKEITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCKATGQVCHALCSPEG

CWGPEPRDCVSCRNVSRGRECVDKCNLLEGEPREFVENSECIQCHPECLPQAMNITCTGRG

PDNCIQCAHYIDGPHCVKTCPAGVMGENNTLVWKYADAGHVCHLCHPNCTYGCTGPGLE

GCPTNGPKIPSIATGMVGALLLLLVVALGIGLFM

FIGURE 5

MLLLVTSLLLCELPHPAFLLIPEVQLVESGGGLVQPGGSLRLSCAASGFDFSRYWMSWVRQA

GMCSFRa signal          CS1scFv

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKESKYGPPCPPCPGGGSSGGGSGGQPREPQVYTLPPSQEEMTK

IgG4 hinge         linker         IgG4

NQVSLTCLVKGFYPSDIAVEWESNGQPENNYKTTPPVLDSDGSFFLYSRLTVDKSRWQEGN
VFSCSVMHEALHNHYTQKSLSLSLGKMALIVLGGVAGLLLFIGLGIFFKRGRKKLLYIFKQPFM

CD4tm                      4-1BB

RPVQTTQEEDGCSCRFPEEEEGGCELGGGRVKFSRSADAPAYQQGQNQLYNELNLGRREEY

Gly3   Zeta

DVLDKRRGRDPEMGGKPRRKNPQEGLYNELQKDKMAEAYSEIGMKGERRRGKGHDGLYQ
GLSTATKDTYDALHMQALPPRLEGGGEGRGSLLTCGDVEENPGPRMLLLVTSLLLCELPHPA

T2A                        EGFRt

FLLIPRKVCNGIGIGEFKDSLSINATNIKHFKNCTSISGDLHILPVAFRGDSFTHTPPLDPQELDIL
KTVKEITGFLLIQAWPENRTDLHAFENLEIIRGRTKQHGQFSLAVVSLNITSLGLRSLKEISDGD
VIISGNKNLCYANTINWKKLFGTSGQKTKIISNRGENSCKATGQVCHALCSPEGCWGPEPRD
CVSCRNVSRGRECVDKCNLLEGEPREFVENSECIQCHPECLPQAMNITCTGRGPDNCIQCAH
YIDGPHCVKTCPAGVMGENNTLVWKYADAGHVCHLCHPNCTYGCTGPGLEGCPTNGPKIP
SIATGMVGALLLLLVVALGIGLFM

FIGURE 6

MLLLVTSLLLCELPHPAFLLIP<u>EVQLVESGGGLVQPGGSLRLSCAASGFDFSRYWMSWVRQA</u>

<u>GMSCFRa</u>          <u>CS1scFV</u>

<u>PGKGLEWIGEINPDSSTINYAPSLKDKFIISRDNAKNSLYLQMNSLRAEDTAVYYCARPDGNY</u>
<u>WYFDVWGQGTLVTVSSGSTSGGGSGGGSGGGGSSDIQMTQSPSSLSASVGDRVTITCKAS</u>
<u>QDVGIAVAWYQQKPGKVPKLLIYWASTRHTGVPDRFSGSGSGTDFTLTISSLQPEDVATYYC</u>
<u>QQYSSYPYTFGQGTKVEIKESK</u>YGPPCPPCPAPEFEGGPSVFLFPPKPKDTLMISRTPEVTCVV

<u>IgG4</u>

VDVSQEDPEVQFNWYVDGVEVHNAKTKPREEQFQSTYRVVSVLTVLHQDWLNGKEYKCK
VSNKGLPSSIEKTISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNHYTQKSLSLSLGK

<u>MALIVLGGVAGLLLFIGLGIFF</u>KRGRKKLLYIFKQPFMRPVQTTQEEDGCSCRFPEEEEGGCEL

<u>CD4tm</u>          <u>4-1BB</u>

<u>GGG</u>RVKFSRSADAPAYQQGQNQLYNELNLGRREEYDVLDKRRGRDPEMGGKPRRKNPQE

<u>Gly3</u>  <u>Zeta</u>

GLYNELQKDKMAEAYSEIGMKGERRRGKGHDGLYQGLSTATKDTYDALHMQALPPR<u>LEGG</u>

<u>T2A</u>

<u>GEGRGSLLTCGDVEENPGP</u>RMLLLVTSLLLCELPHPAFLLIP<u>RKVCNGIGIGEFKDSLSINATNI</u>

<u>EGFt</u>

<u>KHFKNCTSISGDLHILPVAFRGDSFTHTPPLDPQELDILKTVKEITGFLLIQAWPENRTDLHAFE</u>
<u>NLEIIRGRTKQHGQFSLAVVSLNITSLGLRSLKEISDGDVIISGNKNLCYANTINWKKLFGTSGQ</u>
<u>KTKIISNRGENSCKATGQVCHALCSPEGCWGPEPRDCVSCRNVSRGRECVDKCNLLEGEPRE</u>
<u>FVENSECIQCHPECLPQAMNITCTGRGPDNCIQCAHYIDGPHCVKTCPAGVMGENNTLVW</u>
<u>KYADAGHVCHLCHPNCTYGCTGPGLEGCPTNGPKIPSIATGMVGALLLLVVALGIGLFM</u>

FIGURE 7

MLLLVTSLLLCELPHPAFLLIPEVQLVESGGGLVQPGGSLRLSCAASGFDFSRYWMSWVRQA

GMCSFRa                  CS1scFv

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKESKYGPPCPPCPAPEFEGGPSVFLFPPKPKDTLMISRTPEVTCVV

IgG4

VDVSQEDPEVQFNWYVDGVEVHNAKTKPREEQFQSTYRVVSVLTVLHQDWLNGKEYKCK
VSNKGLPSSIEKTISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNHYTQKSLSLSLGK
MFWVLVVVGGVLACYSLLVTVAFIIFWVRSKRSRGGHSDYMNMTPRRPGPTRKHYQPYAP

CD28tm                  CD28cyto

PRDFAAYRSGGGRVKFSRSADAPAYQQGQNQLYNELNLGRREEYDVLDKRRGRDPEMGG

Gly3     Zeta

KPRRKNPQEGLYNELQKDKMAEAYSEIGMKGERRRGKGHDGLYQGLSTATKDTYDALHM
QALPPRLEGGGEGRGSLLTCGDVEENPGPRMLLLVTSLLLCELPHPAFLLIPRKVCNGIGIGEF

T2A                  EGFRt

KDSLSINATNIKHFKNCTSISGDLHILPVAFRGDSFTHTPPLDPQELDILKTVKEITGFLLIQAWP
ENRTDLHAFENLEIIRGRTKQHGQFSLAVVSLNITSLGLRSLKEISDGDVIISGNKNLCYANTIN
WKKLFGTSGQKTKIISNRGENSCKATGQVCHALCSPEGCWGPEPRDCVSCRNVSRGRECVD
KCNLLEGEPREFVENSECIQCHPECLPQAMNITCTGRGPDNCIQCAHYIDGPHCVKTCPAGV
MGENNTLVWKYADAGHVCHLCHPNCTYGCTGPGLEGCPTNGPKIPSIATGMVGALLLLLV
VALGIGLFM

FIGURE 8

MLLLVTSLLLCELPHPAFLLIPEVQLVESGGGLVQPGGSLRLSCAASGFDFSRYWMSWVRQA

GMCSFa            CS1scFv

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKGGGSSGGGSGMALIVLGGVAGLLLFIGLGIFFKRGRKKLLYIFKQ linker       CD4tm              4-1BB

PFMRPVQTTQEEDGCSCRFPEEEEGGCELGGGRVKFSRSADAPAYQQGQNQLYNELNLGR

Gly3   Zeta

REEYDVLDKRRGRDPEMGGKPRRKNPQEGLYNELQKDKMAEAYSEIGMKGERRRGKGHD
GLYQGLSTATKDTYDALHMQALPPRLEGGGEGRGSLLTCGDVEENPGPRMLLLVTSLLLCEL

T2A                EGFRt

PHPAFLLIPRKVCNGIGIGEFKDSLSINATNIKHFKNCTSISGDLHILPVAFRGDSFTHTPPLDPQ
ELDILKTVKEITGFLLIQAWPENRTDLHAFENLEIIRGRTKQHGQFSLAVVSLNITSLGLRSLKEI
SDGDVIISGNKNLCYANTINWKKLFGTSGQKTKIISNRGENSCKATGQVCHALCSPEGCWGP
EPRDCVSCRNVSRGRECVDKCNLLEGEPREFVENSECIQCHPECLPQAMNITCTGRGPDNCI
QCAHYIDGPHCVKTCPAGVMGENNTLVWKYADAGHVCHLCHPNCTYGCTGPGLEGCPTN
GPKIPSIATGMVGALLLLLVVALGIGLFM

FIGURE 9

MLLLVTSLLLCELPHPAFLLIPEVQLVESGGGLVQPGGSLRLSCAASGFDFSRYWMSWVRQA

GMCSFRa			CS1scFv

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKGGGSSGGGSGMFWVLVVVGGVLACYSLLVTVAFIIFWVRSKRS

Linker		CD28tm					CD28cyto

RGGHSDYMNMTPRRPGPTRKHYQPYAPPRDFAAYRSGGGRVKFSRSADAPAYQQGQNQ

Gly3  Zeta

LYNELNLGRREEYDVLDKRRGRDPEMGGKPRRKNPQEGLYNELQKDKMAEAYSEIGMKGE
RRRGKGHDGLYQGLSTATKDTYDALHMQALPPRLEGGGEGRGSLLTCGDVEENPGPRMLL

T2A				EGFRt
LVTSLLLCELPHPAFLLIPRKVCNGIGIGEFKDSLSINATNIKHFKNCTSISGDLHILPVAFRGDSF
THTPPLDPQELDILKTVKEITGFLLIQAWPENRTDLHAFENLEIIRGRTKQHGQFSLAVVSLNIT
SLGLRSLKEISDGDVIISGNKNLCYANTINWKKLFGTSGQKTKIISNRGENSCKATGQVCHALC
SPEGCWGPEPRDCVSCRNVSRGRECVDKCNLLEGEPREFVENSECIQCHPECLPQAMNITC
TGRGPDNCIQCAHYIDGPHCVKTCPAGVMGENNTLVWKYADAGHVCHLCHPNCTYGCTG
PGLEGCPTNGPKIPSIATGMVGALLLLLVVALGIGLFM

SEQUENCE LISTING

<160> NUMBER OF SEQ ID NOS: 46

<210> SEQ ID NO 1
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

```
Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240

Val Glu Ile Lys

<210> SEQ ID NO 2
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Gly Gly Ser Ser Gly Gly Gly Ser Gly
1               5                   10

<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Glu Ser Lys Tyr Gly Pro Pro Cys Pro Pro Cys Pro
1               5                   10

<210> SEQ ID NO 4
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Glu Ser Lys Tyr Gly Pro Pro Cys Pro Ser Cys Pro
1               5                   10

<210> SEQ ID NO 5
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Ser Lys Tyr Gly Pro Pro Cys Pro Pro Cys Pro Gly Gly Gly Ser
1               5                   10                  15

Ser Gly Gly Gly Ser Gly
            20

<210> SEQ ID NO 6
<211> LENGTH: 39
<212> TYPE: PRT
<213> ORGANISM: Homo sapiens
```

-continued

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
            35

<210> SEQ ID NO 7
<211> LENGTH: 48
<212> TYPE: PRT
<213> ORGANISM: Homo sapiens

<400> SEQUENCE: 7

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
            35                  40                  45

<210> SEQ ID NO 8
<211> LENGTH: 45
<212> TYPE: PRT
<213> ORGANISM: Homo sapiens

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 9
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
            35                  40                  45

Cys Leu Val Lys Gly Phe Tyr Pro Ser Asp Ile Ala Val Glu Trp Glu
        50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
            115                 120                 125

Lys

<210> SEQ ID NO 10
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 11
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

```
Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
 50                  55                  60

Glu Val His Gln Ala Lys Thr Lys Pro Arg Glu Glu Gln Phe Gln Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Homo sapiens

<400> SEQUENCE: 13

Leu Cys Tyr Leu Leu Asp Gly Ile Leu Phe Ile Tyr Gly Val Ile Leu
 1               5                  10                  15
```

```
Thr Ala Leu Phe Leu
            20

<210> SEQ ID NO 14
<211> LENGTH: 27
<212> TYPE: PRT
<213> ORGANISM: Homo sapiens

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 15
<211> LENGTH: 28
<212> TYPE: PRT
<213> ORGANISM: Homo sapiens

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 16
<211> LENGTH: 22
<212> TYPE: PRT
<213> ORGANISM: Homo sapiens

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 17
<211> LENGTH: 21
<212> TYPE: PRT
<213> ORGANISM: Homo sapiens

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 18
<211> LENGTH: 23
<212> TYPE: PRT
<213> ORGANISM: Homo sapiens

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 19
<211> LENGTH: 24
<212> TYPE: PRT
<213> ORGANISM: Homo sapiens
```

```
<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 20
<211> LENGTH: 27
<212> TYPE: PRT
<213> ORGANISM: Homo sapiens

<400> SEQUENCE: 20

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 21
<211> LENGTH: 112
<212> TYPE: PRT
<213> ORGANISM: Homo sapiens

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 22
<211> LENGTH: 41
<212> TYPE: PRT
<213> ORGANISM: Homo sapiens

<400> SEQUENCE: 22

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 23
<211> LENGTH: 41
<212> TYPE: PRT
<213> ORGANISM: Homo sapiens

<400> SEQUENCE: 23

Arg Ser Lys Arg Ser Arg Gly Gly His Ser Asp Tyr Met Asn Met Thr
1               5                   10                  15
```

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 24
<211> LENGTH: 42
<212> TYPE: PRT
<213> ORGANISM: Homo sapiens

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 25
<211> LENGTH: 42
<212> TYPE: PRT
<213> ORGANISM: Homo sapiens

<400> SEQUENCE: 25

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
            35                  40

<210> SEQ ID NO 26
<211> LENGTH: 22
<212> TYPE: PRT
<213> ORGANISM: Homo sapiens

<400> SEQUENCE: 26

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 27
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 28
<211> LENGTH: 354
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 28

```
Leu Val Thr Ser Leu Leu Cys Glu Leu Pro His Pro Ala Phe Leu
1               5                   10                  15

Leu Ile Pro Arg Lys Val Cys Asn Gly Ile Gly Ile Gly Glu Phe Lys
            20                  25                  30

Asp Ser Leu Ser Ile Asn Ala Thr Asn Ile Lys His Phe Lys Asn Cys
        35                  40                  45

Thr Ser Ile Ser Gly Asp Leu His Ile Leu Pro Val Ala Phe Arg Gly
50                  55                  60

Asp Ser Phe Thr His Thr Pro Pro Leu Asp Pro Gln Glu Leu Asp Ile
65                  70                  75                  80

Leu Lys Thr Val Lys Glu Ile Thr Gly Phe Leu Leu Ile Gln Ala Trp
                85                  90                  95

Pro Glu Asn Arg Thr Asp Leu His Ala Phe Glu Asn Leu Glu Ile Ile
            100                 105                 110

Arg Gly Arg Thr Lys Gln His Gly Gln Phe Ser Leu Ala Val Val Ser
        115                 120                 125

Leu Asn Ile Thr Ser Leu Gly Leu Arg Ser Leu Lys Glu Ile Ser Asp
130                 135                 140

Gly Asp Val Ile Ile Ser Gly Asn Lys Asn Leu Cys Tyr Ala Asn Thr
145                 150                 155                 160

Ile Asn Trp Lys Lys Leu Phe Gly Thr Ser Gly Gln Lys Thr Lys Ile
                165                 170                 175

Ile Ser Asn Arg Gly Glu Asn Ser Cys Lys Ala Thr Gly Gln Val Cys
            180                 185                 190

His Ala Leu Cys Ser Pro Glu Gly Cys Trp Gly Pro Glu Pro Arg Asp
        195                 200                 205

Cys Val Ser Cys Arg Asn Val Ser Arg Gly Arg Glu Cys Val Asp Lys
210                 215                 220

Cys Asn Leu Leu Glu Gly Glu Pro Arg Glu Phe Val Glu Asn Ser Glu
225                 230                 235                 240

Cys Ile Gln Cys His Pro Glu Cys Leu Pro Gln Ala Met Asn Ile Thr
                245                 250                 255

Cys Thr Gly Arg Gly Pro Asp Asn Cys Ile Gln Cys Ala His Tyr Ile
            260                 265                 270

Asp Gly Pro His Cys Val Lys Thr Cys Pro Ala Gly Val Met Gly Glu
        275                 280                 285

Asn Asn Thr Leu Val Trp Lys Tyr Ala Asp Ala Gly His Val Cys His
290                 295                 300

Leu Cys His Pro Asn Cys Thr Tyr Gly Cys Thr Gly Pro Gly Leu Glu
305                 310                 315                 320

Gly Cys Pro Thr Asn Gly Pro Lys Ile Pro Ser Ile Ala Thr Gly Met
                325                 330                 335

Val Gly Ala Leu Leu Leu Leu Leu Val Val Ala Leu Gly Ile Gly Leu
            340                 345                 350

Phe Met
```

<210> SEQ ID NO 29
<211> LENGTH: 960
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Glu Ser Lys Tyr Gly Pro
            260                 265                 270

Pro Cys Pro Pro Cys Pro Gly Gly Ser Gly Gly Gly Ser Gly
        275                 280                 285

Gly Gln Pro Arg Glu Pro Gln Val Tyr Thr Leu Pro Pro Ser Gln Glu
    290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Arg Leu Thr Val Asp Lys Ser Arg Trp Gln Glu Gly
        355                 360                 365

Asn Val Phe Ser Cys Ser Val Met His Glu Ala Leu His Asn His Tyr
    370                 375                 380
```

-continued

```
Thr Gln Lys Ser Leu Ser Leu Ser Leu Gly Lys Met Phe Trp Val Leu
385                 390                 395                 400

Val Val Val Gly Gly Val Leu Ala Cys Tyr Ser Leu Leu Val Thr Val
            405                 410                 415

Ala Phe Ile Ile Phe Trp Val Arg Ser Lys Arg Ser Arg Gly Gly His
        420                 425                 430

Ser Asp Tyr Met Asn Met Thr Pro Arg Arg Pro Gly Pro Thr Arg Lys
    435                 440                 445

His Tyr Gln Pro Tyr Ala Pro Pro Arg Asp Phe Ala Ala Tyr Arg Ser
450                 455                 460

Gly Gly Gly Arg Val Lys Phe Ser Arg Ser Ala Asp Ala Pro Ala Tyr
465                 470                 475                 480

Gln Gln Gly Gln Asn Gln Leu Tyr Asn Glu Leu Asn Leu Gly Arg Arg
            485                 490                 495

Glu Glu Tyr Asp Val Leu Asp Lys Arg Arg Gly Arg Asp Pro Glu Met
            500                 505                 510

Gly Gly Lys Pro Arg Arg Lys Asn Pro Gln Glu Gly Leu Tyr Asn Glu
        515                 520                 525

Leu Gln Lys Asp Lys Met Ala Glu Ala Tyr Ser Glu Ile Gly Met Lys
    530                 535                 540

Gly Glu Arg Arg Arg Gly Lys Gly His Asp Gly Leu Tyr Gln Gly Leu
545                 550                 555                 560

Ser Thr Ala Thr Lys Asp Thr Tyr Asp Ala Leu His Met Gln Ala Leu
            565                 570                 575

Pro Pro Arg Leu Glu Gly Gly Gly Glu Gly Arg Gly Ser Leu Leu Thr
            580                 585                 590

Cys Gly Asp Val Glu Glu Asn Pro Gly Pro Arg Met Leu Leu Leu Val
        595                 600                 605

Thr Ser Leu Leu Leu Cys Glu Leu Pro His Pro Ala Phe Leu Leu Ile
    610                 615                 620

Pro Arg Lys Val Cys Asn Gly Ile Gly Ile Gly Glu Phe Lys Asp Ser
625                 630                 635                 640

Leu Ser Ile Asn Ala Thr Asn Ile Lys His Phe Lys Asn Cys Thr Ser
            645                 650                 655

Ile Ser Gly Asp Leu His Ile Leu Pro Val Ala Phe Arg Gly Asp Ser
            660                 665                 670

Phe Thr His Thr Pro Pro Leu Asp Pro Gln Glu Leu Asp Ile Leu Lys
        675                 680                 685

Thr Val Lys Glu Ile Thr Gly Phe Leu Leu Ile Gln Ala Trp Pro Glu
    690                 695                 700

Asn Arg Thr Asp Leu His Ala Phe Glu Asn Leu Glu Ile Ile Arg Gly
705                 710                 715                 720

Arg Thr Lys Gln His Gly Gln Phe Ser Leu Ala Val Val Ser Leu Asn
            725                 730                 735

Ile Thr Ser Leu Gly Leu Arg Ser Leu Lys Glu Ile Ser Asp Gly Asp
            740                 745                 750

Val Ile Ile Ser Gly Asn Lys Asn Leu Cys Tyr Ala Asn Thr Ile Asn
        755                 760                 765

Trp Lys Lys Leu Phe Gly Thr Ser Gly Gln Lys Thr Lys Ile Ile Ser
    770                 775                 780

Asn Arg Gly Glu Asn Ser Cys Lys Ala Thr Gly Gln Val Cys His Ala
785                 790                 795                 800

Leu Cys Ser Pro Glu Gly Cys Trp Gly Pro Glu Pro Arg Asp Cys Val
```

```
            805                 810                 815

Ser Cys Arg Asn Val Ser Arg Gly Arg Glu Cys Val Asp Lys Cys Asn
            820                 825                 830

Leu Leu Glu Gly Glu Pro Arg Glu Phe Val Glu Asn Ser Glu Cys Ile
            835                 840                 845

Gln Cys His Pro Glu Cys Leu Pro Gln Ala Met Asn Ile Thr Cys Thr
            850                 855                 860

Gly Arg Gly Pro Asp Asn Cys Ile Gln Cys Ala His Tyr Ile Asp Gly
865                 870                 875                 880

Pro His Cys Val Lys Thr Cys Pro Ala Gly Val Met Gly Glu Asn Asn
            885                 890                 895

Thr Leu Val Trp Lys Tyr Ala Asp Ala Gly His Val Cys His Leu Cys
            900                 905                 910

His Pro Asn Cys Thr Tyr Gly Cys Thr Gly Pro Gly Leu Glu Gly Cys
            915                 920                 925

Pro Thr Asn Gly Pro Lys Ile Pro Ser Ile Ala Thr Gly Met Val Gly
            930                 935                 940

Ala Leu Leu Leu Leu Leu Val Val Ala Leu Gly Ile Gly Leu Phe Met
945                 950                 955                 960

<210> SEQ ID NO 30
<211> LENGTH: 579
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
            85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
            165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205
```

```
Trp Ala Ser Thr Arg His Thr Gly Val Pro Asp Arg Phe Ser Gly Ser
    210                 215                 220
Gly Ser Gly Thr Asp Phe Thr Leu Thr Ile Ser Ser Leu Gln Pro Glu
225                 230                 235                 240
Asp Val Ala Thr Tyr Tyr Cys Gln Gln Tyr Ser Ser Tyr Pro Tyr Thr
                245                 250                 255
Phe Gly Gln Gly Thr Lys Val Glu Ile Lys Glu Ser Lys Tyr Gly Pro
            260                 265                 270
Pro Cys Pro Pro Cys Pro Gly Gly Ser Gly Gly Gly Ser Gly
        275                 280                 285
Gly Gln Pro Arg Glu Pro Gln Val Tyr Thr Leu Pro Pro Ser Gln Glu
    290                 295                 300
Glu Met Thr Lys Asn Gln Val Ser Leu Thr Cys Leu Val Lys Gly Phe
305                 310                 315                 320
Tyr Pro Ser Asp Ile Ala Val Glu Trp Glu Ser Asn Gly Gln Pro Glu
                325                 330                 335
Asn Asn Tyr Lys Thr Thr Pro Pro Val Leu Asp Ser Asp Gly Ser Phe
            340                 345                 350
Phe Leu Tyr Ser Arg Leu Thr Val Asp Lys Ser Arg Trp Gln Glu Gly
        355                 360                 365
Asn Val Phe Ser Cys Ser Val Met His Glu Ala Leu His Asn His Tyr
    370                 375                 380
Thr Gln Lys Ser Leu Ser Leu Ser Leu Gly Lys Met Phe Trp Val Leu
385                 390                 395                 400
Val Val Val Gly Gly Val Leu Ala Cys Tyr Ser Leu Leu Val Thr Val
                405                 410                 415
Ala Phe Ile Ile Phe Trp Val Arg Ser Lys Arg Ser Arg Gly Gly His
            420                 425                 430
Ser Asp Tyr Met Asn Met Thr Pro Arg Arg Pro Gly Pro Thr Arg Lys
        435                 440                 445
His Tyr Gln Pro Tyr Ala Pro Pro Arg Asp Phe Ala Ala Tyr Arg Ser
    450                 455                 460
Gly Gly Gly Arg Val Lys Phe Ser Arg Ser Ala Asp Ala Pro Ala Tyr
465                 470                 475                 480
Gln Gln Gly Gln Asn Gln Leu Tyr Asn Glu Leu Asn Leu Gly Arg Arg
                485                 490                 495
Glu Glu Tyr Asp Val Leu Asp Lys Arg Arg Gly Arg Asp Pro Glu Met
            500                 505                 510
Gly Gly Lys Pro Arg Arg Lys Asn Pro Gln Glu Gly Leu Tyr Asn Glu
        515                 520                 525
Leu Gln Lys Asp Lys Met Ala Glu Ala Tyr Ser Glu Ile Gly Met Lys
    530                 535                 540
Gly Glu Arg Arg Arg Gly Lys Gly His Asp Gly Leu Tyr Gln Gly Leu
545                 550                 555                 560
Ser Thr Ala Thr Lys Asp Thr Tyr Asp Ala Leu His Met Gln Ala Leu
                565                 570                 575
Pro Pro Arg

<210> SEQ ID NO 31
<211> LENGTH: 557
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic polypeptide"

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240

Val Glu Ile Lys Glu Ser Lys Tyr Gly Pro Pro Cys Pro Pro Cys Pro
                245                 250                 255

Gly Gly Gly Ser Ser Gly Gly Ser Gly Gly Gln Pro Arg Glu Pro
            260                 265                 270

Gln Val Tyr Thr Leu Pro Pro Ser Gln Glu Glu Met Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Tyr Lys Thr Thr
305                 310                 315                 320

Pro Pro Val Leu Asp Ser Asp Gly Ser Phe Phe Leu Tyr Ser Arg Leu
                325                 330                 335

Thr Val Asp Lys Ser Arg Trp Gln Glu Gly Asn Val Phe Ser Cys Ser
            340                 345                 350

Val Met His Glu Ala Leu His Asn His Tyr Thr Gln Lys Ser Leu Ser
        355                 360                 365

Leu Ser Leu Gly Lys Met Phe Trp Val Leu Val Val Val Gly Gly Val
    370                 375                 380

Leu Ala Cys Tyr Ser Leu Leu Val Thr Val Ala Phe Ile Ile Phe Trp
385                 390                 395                 400
```

-continued

Val Arg Ser Lys Arg Ser Arg Gly Gly His Ser Asp Tyr Met Asn Met
                405                 410                 415

Thr Pro Arg Arg Pro Gly Pro Thr Arg Lys His Tyr Gln Pro Tyr Ala
            420                 425                 430

Pro Pro Arg Asp Phe Ala Ala Tyr Arg Ser Gly Gly Gly Arg Val Lys
            435                 440                 445

Phe Ser Arg Ser Ala Asp Ala Pro Ala Tyr Gln Gln Gly Gln Asn Gln
450                 455                 460

Leu Tyr Asn Glu Leu Asn Leu Gly Arg Arg Glu Glu Tyr Asp Val Leu
465                 470                 475                 480

Asp Lys Arg Arg Gly Arg Asp Pro Glu Met Gly Gly Lys Pro Arg Arg
                485                 490                 495

Lys Asn Pro Gln Glu Gly Leu Tyr Asn Glu Leu Gln Lys Asp Lys Met
                500                 505                 510

Ala Glu Ala Tyr Ser Glu Ile Gly Met Lys Gly Glu Arg Arg Arg Gly
            515                 520                 525

Lys Gly His Asp Gly Leu Tyr Gln Gly Leu Ser Thr Ala Thr Lys Asp
            530                 535                 540

Thr Tyr Asp Ala Leu His Met Gln Ala Leu Pro Pro Arg
545                 550                 555

<210> SEQ ID NO 32
<211> LENGTH: 955
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 32

Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Asp Phe Ser Arg Tyr Trp Met Ser Trp Val Arg Gln Ala Pro Gly
50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
                100                 105                 110

Thr Ala Val Tyr Tyr Cys Ala Arg Pro Asp Gly Asn Tyr Trp Tyr Phe
            115                 120                 125

Asp Val Trp Gly Gln Gly Thr Leu Val Thr Val Ser Ser Gly Ser Thr
130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

```
Ala Trp Tyr Gln Gln Lys Pro Gly Lys Val Pro Lys Leu Leu Ile Tyr
        195                 200                 205
Trp Ala Ser Thr Arg His Thr Gly Val Pro Asp Arg Phe Ser Gly Ser
    210                 215                 220
Gly Ser Gly Thr Asp Phe Thr Leu Thr Ile Ser Ser Leu Gln Pro Glu
225                 230                 235                 240
Asp Val Ala Thr Tyr Tyr Cys Gln Gln Tyr Ser Ser Tyr Pro Tyr Thr
                245                 250                 255
Phe Gly Gln Gly Thr Lys Val Glu Ile Lys Glu Ser Lys Tyr Gly Pro
                260                 265                 270
Pro Cys Pro Pro Cys Pro Gly Gly Ser Ser Gly Gly Gly Ser Gly
            275                 280                 285
Gly Gln Pro Arg Glu Pro Gln Val Tyr Thr Leu Pro Pro Ser Gln Glu
    290                 295                 300
Glu Met Thr Lys Asn Gln Val Ser Leu Thr Cys Leu Val Lys Gly Phe
305                 310                 315                 320
Tyr Pro Ser Asp Ile Ala Val Glu Trp Glu Ser Asn Gly Gln Pro Glu
                325                 330                 335
Asn Asn Tyr Lys Thr Thr Pro Pro Val Leu Asp Ser Asp Gly Ser Phe
                340                 345                 350
Phe Leu Tyr Ser Arg Leu Thr Val Asp Lys Ser Arg Trp Gln Glu Gly
                355                 360                 365
Asn Val Phe Ser Cys Ser Val Met His Glu Ala Leu His Asn His Tyr
            370                 375                 380
Thr Gln Lys Ser Leu Ser Leu Ser Leu Gly Lys Met Ala Leu Ile Val
385                 390                 395                 400
Leu Gly Gly Val Ala Gly Leu Leu Leu Phe Ile Gly Leu Gly Ile Phe
                405                 410                 415
Phe Lys Arg Gly Arg Lys Lys Leu Leu Tyr Ile Phe Lys Gln Pro Phe
                420                 425                 430
Met Arg Pro Val Gln Thr Thr Gln Glu Glu Asp Gly Cys Ser Cys Arg
            435                 440                 445
Phe Pro Glu Glu Glu Glu Gly Gly Cys Glu Leu Gly Gly Gly Arg Val
450                 455                 460
Lys Phe Ser Arg Ser Ala Asp Ala Pro Ala Tyr Gln Gln Gly Gln Asn
465                 470                 475                 480
Gln Leu Tyr Asn Glu Leu Asn Leu Gly Arg Arg Glu Glu Tyr Asp Val
                485                 490                 495
Leu Asp Lys Arg Arg Gly Arg Asp Pro Glu Met Gly Gly Lys Pro Arg
            500                 505                 510
Arg Lys Asn Pro Gln Glu Gly Leu Tyr Asn Glu Leu Gln Lys Asp Lys
            515                 520                 525
Met Ala Glu Ala Tyr Ser Glu Ile Gly Met Lys Gly Glu Arg Arg Arg
530                 535                 540
Gly Lys Gly His Asp Gly Leu Tyr Gln Gly Leu Ser Thr Ala Thr Lys
545                 550                 555                 560
Asp Thr Tyr Asp Ala Leu His Met Gln Ala Leu Pro Pro Arg Leu Glu
                565                 570                 575
Gly Gly Gly Glu Gly Arg Gly Ser Leu Leu Thr Cys Gly Asp Val Glu
            580                 585                 590
Glu Asn Pro Gly Pro Arg Met Leu Leu Leu Val Thr Ser Leu Leu Leu
            595                 600                 605
Cys Glu Leu Pro His Pro Ala Phe Leu Leu Ile Pro Arg Lys Val Cys
```

Asn Gly Ile Gly Ile Gly Glu Phe Lys Asp Ser Leu Ser Ile Asn Ala
625                 630                 635                 640

Thr Asn Ile Lys His Phe Lys Asn Cys Thr Ser Ile Ser Gly Asp Leu
            645                 650                 655

His Ile Leu Pro Val Ala Phe Arg Gly Asp Ser Phe Thr His Thr Pro
        660                 665                 670

Pro Leu Asp Pro Gln Glu Leu Asp Ile Leu Lys Thr Val Lys Glu Ile
    675                 680                 685

Thr Gly Phe Leu Leu Ile Gln Ala Trp Pro Glu Asn Arg Thr Asp Leu
690                 695                 700

His Ala Phe Glu Asn Leu Glu Ile Ile Arg Gly Arg Thr Lys Gln His
705                 710                 715                 720

Gly Gln Phe Ser Leu Ala Val Val Ser Leu Asn Ile Thr Ser Leu Gly
                725                 730                 735

Leu Arg Ser Leu Lys Glu Ile Ser Asp Gly Asp Val Ile Ile Ser Gly
            740                 745                 750

Asn Lys Asn Leu Cys Tyr Ala Asn Thr Ile Asn Trp Lys Lys Leu Phe
        755                 760                 765

Gly Thr Ser Gly Gln Lys Thr Lys Ile Ile Ser Asn Arg Gly Glu Asn
    770                 775                 780

Ser Cys Lys Ala Thr Gly Gln Val Cys His Ala Leu Cys Ser Pro Glu
785                 790                 795                 800

Gly Cys Trp Gly Pro Glu Pro Arg Asp Cys Val Ser Cys Arg Asn Val
                805                 810                 815

Ser Arg Gly Arg Glu Cys Val Asp Lys Cys Asn Leu Leu Glu Gly Glu
            820                 825                 830

Pro Arg Glu Phe Val Glu Asn Ser Glu Cys Ile Gln Cys His Pro Glu
        835                 840                 845

Cys Leu Pro Gln Ala Met Asn Ile Thr Cys Thr Gly Arg Gly Pro Asp
    850                 855                 860

Asn Cys Ile Gln Cys Ala His Tyr Ile Asp Gly Pro His Cys Val Lys
865                 870                 875                 880

Thr Cys Pro Ala Gly Val Met Gly Glu Asn Asn Thr Leu Val Trp Lys
                885                 890                 895

Tyr Ala Asp Ala Gly His Val Cys His Leu Cys His Pro Asn Cys Thr
            900                 905                 910

Tyr Gly Cys Thr Gly Pro Gly Leu Glu Gly Cys Pro Thr Asn Gly Pro
        915                 920                 925

Lys Ile Pro Ser Ile Ala Thr Gly Met Val Gly Ala Leu Leu Leu Leu
    930                 935                 940

Leu Val Val Ala Leu Gly Ile Gly Leu Phe Met
945                 950                 955

<210> SEQ ID NO 33
<211> LENGTH: 574
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
            165                 170                 175

Arg Val Thr Ile Thr Cys Lys Ala Ser Gln Asp Val Gly Ile Ala Val
        180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
            245                 250                 255

Phe Gly Gln Gly Thr Lys Val Glu Ile Lys Glu Ser Lys Tyr Gly Pro
        260                 265                 270

Pro Cys Pro Pro Cys Pro Gly Gly Gly Ser Ser Gly Gly Gly Ser Gly
        275                 280                 285

Gly Gln Pro Arg Glu Pro Gln Val Tyr Thr Leu Pro Pro Ser Gln Glu
290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
            325                 330                 335

Asn Asn Tyr Lys Thr Thr Pro Pro Val Leu Asp Ser Asp Gly Ser Phe
        340                 345                 350

Phe Leu Tyr Ser Arg Leu Thr Val Asp Lys Ser Arg Trp Gln Glu Gly
        355                 360                 365

Asn Val Phe Ser Cys Ser Val Met His Glu Ala Leu His Asn His Tyr
370                 375                 380

Thr Gln Lys Ser Leu Ser Leu Ser Leu Gly Lys Met Ala Leu Ile Val
385                 390                 395                 400

Leu Gly Gly Val Ala Gly Leu Leu Leu Phe Ile Gly Leu Gly Ile Phe
            405                 410                 415

Phe Lys Arg Gly Arg Lys Lys Leu Leu Tyr Ile Phe Lys Gln Pro Phe
        420                 425                 430

Met Arg Pro Val Gln Thr Thr Gln Glu Asp Gly Cys Ser Cys Arg
            435                 440                 445

Phe Pro Glu Glu Glu Gly Gly Cys Glu Leu Gly Gly Gly Arg Val
450                 455                 460

Lys Phe Ser Arg Ser Ala Asp Ala Pro Ala Tyr Gln Gln Gly Gln Asn
465                 470                 475                 480

Gln Leu Tyr Asn Glu Leu Asn Leu Gly Arg Arg Glu Glu Tyr Asp Val
                485                 490                 495

Leu Asp Lys Arg Arg Gly Arg Asp Pro Glu Met Gly Gly Lys Pro Arg
            500                 505                 510

Arg Lys Asn Pro Gln Glu Gly Leu Tyr Asn Glu Leu Gln Lys Asp Lys
            515                 520                 525

Met Ala Glu Ala Tyr Ser Glu Ile Gly Met Lys Gly Glu Arg Arg Arg
530                 535                 540

Gly Lys Gly His Asp Gly Leu Tyr Gln Gly Leu Ser Thr Ala Thr Lys
545                 550                 555                 560

Asp Thr Tyr Asp Ala Leu His Met Gln Ala Leu Pro Pro Arg
                565                 570

<210> SEQ ID NO 34
<211> LENGTH: 552
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr 210                 215                 220
Cys Gln Gln Tyr Ser Ser Tyr Pro Tyr Thr Phe Gly Gln Gly Thr Lys
225                 230                 235                 240

Val Glu Ile Lys Glu Ser Lys Tyr Gly Pro Pro Cys Pro Pro Cys Pro
                245                 250                 255

Gly Gly Gly Ser Ser Gly Gly Ser Gly Gly Gln Pro Arg Glu Pro
            260                 265                 270

Gln Val Tyr Thr Leu Pro Pro Ser Gln Glu Glu Met Thr Lys Asn Gln
                275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Arg Leu
                325                 330                 335

Thr Val Asp Lys Ser Arg Trp Gln Glu Gly Asn Val Phe Ser Cys Ser
                340                 345                 350

Val Met His Glu Ala Leu His Asn His Tyr Thr Gln Lys Ser Leu Ser
                355                 360                 365

Leu Ser Leu Gly Lys Met Ala Leu Ile Val Leu Gly Gly Val Ala Gly
370                 375                 380

Leu Leu Leu Phe Ile Gly Leu Gly Ile Phe Phe Lys Arg Gly Arg Lys
385                 390                 395                 400

Lys Leu Leu Tyr Ile Phe Lys Gln Pro Phe Met Arg Pro Val Gln Thr
                405                 410                 415

Thr Gln Glu Glu Asp Gly Cys Ser Cys Arg Phe Pro Glu Glu Glu Glu
                420                 425                 430

Gly Gly Cys Glu Leu Gly Gly Gly Arg Val Lys Phe Ser Arg Ser Ala
                435                 440                 445

Asp Ala Pro Ala Tyr Gln Gln Gly Gln Asn Gln Leu Tyr Asn Glu Leu
450                 455                 460

Asn Leu Gly Arg Arg Glu Glu Tyr Asp Val Leu Asp Lys Arg Arg Gly
465                 470                 475                 480

Arg Asp Pro Glu Met Gly Gly Lys Pro Arg Arg Lys Asn Pro Gln Glu
                485                 490                 495

Gly Leu Tyr Asn Glu Leu Gln Lys Asp Lys Met Ala Glu Ala Tyr Ser
                500                 505                 510

Glu Ile Gly Met Lys Gly Glu Arg Arg Arg Gly Lys Gly His Asp Gly
                515                 520                 525

Leu Tyr Gln Gly Leu Ser Thr Ala Thr Lys Asp Thr Tyr Asp Ala Leu
530                 535                 540

His Met Gln Ala Leu Pro Pro Arg
545                 550

<210> SEQ ID NO 35
<211> LENGTH: 1055
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Met Leu Leu Leu Val Thr Ser Leu Leu Leu Cys Glu Leu Pro His Pro
1               5                   10                  15

```
Ala Phe Leu Leu Ile Pro Glu Val Gln Leu Val Glu Ser Gly Gly
                20              25              30
Leu Val Gln Pro Gly Gly Ser Leu Arg Leu Ser Cys Ala Ala Ser Gly
            35              40              45
Phe Asp Phe Ser Arg Tyr Trp Met Ser Val Arg Gln Ala Pro Gly
 50              55              60
Lys Gly Leu Glu Trp Ile Gly Glu Ile Asn Pro Asp Ser Ser Thr Ile
65              70              75              80
Asn Tyr Ala Pro Ser Leu Lys Asp Lys Phe Ile Ile Ser Arg Asp Asn
                85              90              95
Ala Lys Asn Ser Leu Tyr Leu Gln Met Asn Ser Leu Arg Ala Glu Asp
            100             105             110
Thr Ala Val Tyr Tyr Cys Ala Arg Pro Asp Gly Asn Tyr Trp Tyr Phe
            115             120             125
Asp Val Trp Gly Gln Gly Thr Leu Val Thr Val Ser Ser Gly Ser Thr
130             135             140
Ser Gly Gly Gly Ser Gly Gly Gly Ser Gly Gly Gly Ser Ser Asp
145             150             155             160
Ile Gln Met Thr Gln Ser Pro Ser Ser Leu Ser Ala Ser Val Gly Asp
                165             170             175
Arg Val Thr Ile Thr Cys Lys Ala Ser Gln Asp Val Gly Ile Ala Val
            180             185             190
Ala Trp Tyr Gln Gln Lys Pro Gly Lys Val Pro Lys Leu Leu Ile Tyr
            195             200             205
Trp Ala Ser Thr Arg His Thr Gly Val Pro Asp Arg Phe Ser Gly Ser
210             215             220
Gly Ser Gly Thr Asp Phe Thr Leu Thr Ile Ser Ser Leu Gln Pro Glu
225             230             235             240
Asp Val Ala Thr Tyr Tyr Cys Gln Gln Tyr Ser Ser Tyr Pro Tyr Thr
            245             250             255
Phe Gly Gln Gly Thr Lys Val Glu Ile Lys Glu Ser Lys Tyr Gly Pro
            260             265             270
Pro Cys Pro Pro Cys Pro Ala Pro Glu Phe Glu Gly Gly Pro Ser Val
        275             280             285
Phe Leu Phe Pro Pro Lys Pro Lys Asp Thr Leu Met Ile Ser Arg Thr
290             295             300
Pro Glu Val Thr Cys Val Val Asp Val Ser Gln Glu Asp Pro Glu
305             310             315             320
Val Gln Phe Asn Trp Tyr Val Asp Gly Val Glu Val His Asn Ala Lys
            325             330             335
Thr Lys Pro Arg Glu Glu Gln Phe Gln Ser Thr Tyr Arg Val Val Ser
            340             345             350
Val Leu Thr Val Leu His Gln Asp Trp Leu Asn Gly Lys Glu Tyr Lys
            355             360             365
Cys Lys Val Ser Asn Lys Gly Leu Pro Ser Ser Ile Glu Lys Thr Ile
        370             375             380
Ser Lys Ala Lys Gly Gln Pro Arg Glu Pro Gln Val Tyr Thr Leu Pro
385             390             395             400
Pro Ser Gln Glu Glu Met Thr Lys Asn Gln Val Ser Leu Thr Cys Leu
                405             410             415
Val Lys Gly Phe Tyr Pro Ser Asp Ile Ala Val Glu Trp Glu Ser Asn
            420             425             430
```

-continued

```
Gly Gln Pro Glu Asn Asn Tyr Lys Thr Thr Pro Pro Val Leu Asp Ser
        435                 440                 445

Asp Gly Ser Phe Phe Leu Tyr Ser Arg Leu Thr Val Asp Lys Ser Arg
450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Met
            485                 490                 495

Ala Leu Ile Val Leu Gly Gly Val Ala Gly Leu Leu Leu Phe Ile Gly
            500                 505                 510

Leu Gly Ile Phe Phe Lys Arg Gly Arg Lys Lys Leu Leu Tyr Ile Phe
            515                 520                 525

Lys Gln Pro Phe Met Arg Pro Val Gln Thr Thr Gln Glu Glu Asp Gly
        530                 535                 540

Cys Ser Cys Arg Phe Pro Glu Glu Glu Glu Gly Gly Cys Glu Leu Gly
545                 550                 555                 560

Gly Gly Arg Val Lys Phe Ser Arg Ser Ala Asp Ala Pro Ala Tyr Gln
                565                 570                 575

Gln Gly Gln Asn Gln Leu Tyr Asn Glu Leu Asn Leu Gly Arg Arg Glu
            580                 585                 590

Glu Tyr Asp Val Leu Asp Lys Arg Arg Gly Arg Asp Pro Glu Met Gly
            595                 600                 605

Gly Lys Pro Arg Arg Lys Asn Pro Gln Glu Gly Leu Tyr Asn Glu Leu
        610                 615                 620

Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
                645                 650                 655

Thr Ala Thr Lys Asp Thr Tyr Asp Ala Leu His Met Gln Ala Leu Pro
            660                 665                 670

Pro Arg Leu Glu Gly Gly Gly Glu Gly Arg Gly Ser Leu Leu Thr Cys
        675                 680                 685

Gly Asp Val Glu Glu Asn Pro Gly Pro Arg Met Leu Leu Leu Val Thr
690                 695                 700

Ser Leu Leu Leu Cys Glu Leu Pro His Pro Ala Phe Leu Leu Ile Pro
705                 710                 715                 720

Arg Lys Val Cys Asn Gly Ile Gly Ile Gly Glu Phe Lys Asp Ser Leu
                725                 730                 735

Ser Ile Asn Ala Thr Asn Ile Lys His Phe Lys Asn Cys Thr Ser Ile
            740                 745                 750

Ser Gly Asp Leu His Ile Leu Pro Val Ala Phe Arg Gly Asp Ser Phe
            755                 760                 765

Thr His Thr Pro Pro Leu Asp Pro Gln Glu Leu Asp Ile Leu Lys Thr
        770                 775                 780

Val Lys Glu Ile Thr Gly Phe Leu Leu Ile Gln Ala Trp Pro Glu Asn
785                 790                 795                 800

Arg Thr Asp Leu His Ala Phe Glu Asn Leu Glu Ile Ile Arg Gly Arg
                805                 810                 815

Thr Lys Gln His Gly Gln Phe Ser Leu Ala Val Val Ser Leu Asn Ile
            820                 825                 830

Thr Ser Leu Gly Leu Arg Ser Leu Lys Glu Ile Ser Asp Gly Asp Val
            835                 840                 845

Ile Ile Ser Gly Asn Lys Asn Leu Cys Tyr Ala Asn Thr Ile Asn Trp
```

```
                850                 855                 860
Lys Lys Leu Phe Gly Thr Ser Gly Gln Lys Thr Lys Ile Ile Ser Asn
865                 870                 875                 880

Arg Gly Glu Asn Ser Cys Lys Ala Thr Gly Gln Val Cys His Ala Leu
                885                 890                 895

Cys Ser Pro Glu Gly Cys Trp Gly Pro Glu Pro Arg Asp Cys Val Ser
                900                 905                 910

Cys Arg Asn Val Ser Arg Gly Arg Glu Cys Val Asp Lys Cys Asn Leu
                915                 920                 925

Leu Glu Gly Glu Pro Arg Glu Phe Val Glu Asn Ser Glu Cys Ile Gln
                930                 935                 940

Cys His Pro Glu Cys Leu Pro Gln Ala Met Asn Ile Thr Cys Thr Gly
945                 950                 955                 960

Arg Gly Pro Asp Asn Cys Ile Gln Cys Ala His Tyr Ile Asp Gly Pro
                965                 970                 975

His Cys Val Lys Thr Cys Pro Ala Gly Val Met Gly Glu Asn Asn Thr
                980                 985                 990

Leu Val Trp Lys Tyr Ala Asp Ala  Gly His Val Cys His  Leu Cys His
                995                 1000                1005

Pro Asn  Cys Thr Tyr Gly Cys  Thr Gly Pro Gly Leu  Glu Gly Cys
                1010                1015                1020

Pro Thr  Asn Gly Pro Lys Ile  Pro Ser Ile Ala Thr  Gly Met Val
                1025                1030                1035

Gly Ala  Leu Leu Leu Leu Leu  Val Val Ala Leu Gly  Ile Gly Leu
                1040                1045                1050

Phe Met
1055

<210> SEQ ID NO 36
<211> LENGTH: 674
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
                100                 105                 110

Thr Ala Val Tyr Tyr Cys Ala Arg Pro Asp Gly Asn Tyr Trp Tyr Phe
            115                 120                 125

Asp Val Trp Gly Gln Gly Thr Leu Val Thr Val Ser Ser Gly Ser Thr
        130                 135                 140
```

```
Ser Gly Gly Gly Ser Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Glu Ser Lys Tyr Gly Pro
            260                 265                 270

Pro Cys Pro Pro Cys Pro Ala Pro Glu Phe Glu Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Gln Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Gly Leu Pro Ser Ser Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Arg Leu Thr Val Asp Lys Ser Arg
    450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Met
                485                 490                 495

Ala Leu Ile Val Leu Gly Gly Val Ala Gly Leu Leu Leu Phe Ile Gly
            500                 505                 510

Leu Gly Ile Phe Phe Lys Arg Gly Arg Lys Lys Leu Leu Tyr Ile Phe
        515                 520                 525

Lys Gln Pro Phe Met Arg Pro Val Gln Thr Thr Gln Glu Glu Asp Gly
    530                 535                 540

Cys Ser Cys Arg Phe Pro Glu Glu Glu Glu Gly Gly Cys Glu Leu Gly
545                 550                 555                 560
```

-continued

```
Gly Gly Arg Val Lys Phe Ser Arg Ser Ala Asp Ala Pro Ala Tyr Gln
                565                 570                 575

Gln Gly Gln Asn Gln Leu Tyr Asn Glu Leu Asn Leu Gly Arg Arg Glu
            580                 585                 590

Glu Tyr Asp Val Leu Asp Lys Arg Arg Gly Arg Asp Pro Glu Met Gly
        595                 600                 605

Gly Lys Pro Arg Arg Lys Asn Pro Gln Glu Gly Leu Tyr Asn Glu Leu
    610                 615                 620

Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
                645                 650                 655

Thr Ala Thr Lys Asp Thr Tyr Asp Ala Leu His Met Gln Ala Leu Pro
            660                 665                 670

Pro Arg

<210> SEQ ID NO 37
<211> LENGTH: 652
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240
```

-continued

```
Val Glu Ile Lys Glu Ser Lys Tyr Gly Pro Pro Cys Pro Pro Cys Pro
                245                 250                 255

Ala Pro Glu Phe Glu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser Gln Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Gln Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Gly Leu Pro Ser Ser Ile Glu Lys Thr Ile Ser Lys Ala Lys Gly Gln
        355                 360                 365

Pro Arg Glu Pro Gln Val Tyr Thr Leu Pro Pro Ser Gln Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Arg Leu Thr Val Asp Lys Ser Arg Trp Gln Glu Gly Asn Val
        435                 440                 445

Phe Ser Cys Ser Val Met His Glu Ala Leu His Asn His Tyr Thr Gln
    450                 455                 460

Lys Ser Leu Ser Leu Ser Leu Gly Lys Met Ala Leu Ile Val Leu Gly
465                 470                 475                 480

Gly Val Ala Gly Leu Leu Leu Phe Ile Gly Leu Gly Ile Phe Phe Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
        515                 520                 525

Glu Glu Glu Glu Gly Gly Cys Glu Leu Gly Gly Gly Arg Val Lys Phe
    530                 535                 540

Ser Arg Ser Ala Asp Ala Pro Ala Tyr Gln Gln Gly Gln Asn Gln Leu
545                 550                 555                 560

Tyr Asn Glu Leu Asn Leu Gly Arg Arg Glu Glu Tyr Asp Val Leu Asp
                565                 570                 575

Lys Arg Arg Gly Arg Asp Pro Glu Met Gly Gly Lys Pro Arg Arg Lys
            580                 585                 590

Asn Pro Gln Glu Gly Leu Tyr Asn Glu Leu Gln Lys Asp Lys Met Ala
        595                 600                 605

Glu Ala Tyr Ser Glu Ile Gly Met Lys Gly Glu Arg Arg Arg Gly Lys
    610                 615                 620

Gly His Asp Gly Leu Tyr Gln Gly Leu Ser Thr Ala Thr Lys Asp Thr
625                 630                 635                 640

Tyr Asp Ala Leu His Met Gln Ala Leu Pro Pro Arg
                645                 650
```

```
<210> SEQ ID NO 38
<211> LENGTH: 1060
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
            35                  40                  45

Phe Asp Phe Ser Arg Tyr Trp Met Ser Trp Val Arg Gln Ala Pro Gly
        50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
            115                 120                 125

Asp Val Trp Gly Gln Gly Thr Leu Val Thr Val Ser Ser Gly Ser Thr
        130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
            195                 200                 205

Trp Ala Ser Thr Arg His Thr Gly Val Pro Asp Arg Phe Ser Gly Ser
        210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Glu Ser Lys Tyr Gly Pro
            260                 265                 270

Pro Cys Pro Pro Cys Pro Ala Pro Glu Phe Glu Gly Gly Pro Ser Val
            275                 280                 285

Phe Leu Phe Pro Pro Lys Pro Lys Asp Thr Leu Met Ile Ser Arg Thr
        290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Gln Ser Thr Tyr Arg Val Val Ser
            340                 345                 350

Val Leu Thr Val Leu His Gln Asp Trp Leu Asn Gly Lys Glu Tyr Lys
```

```
                355                 360                 365
Cys Lys Val Ser Asn Lys Gly Leu Pro Ser Ser Ile Glu Lys Thr Ile
        370                 375                 380
Ser Lys Ala Lys Gly Gln Pro Arg Glu Pro Gln Val Tyr Thr Leu Pro
385                 390                 395                 400
Pro Ser Gln Glu Glu Met Thr Lys Asn Gln Val Ser Leu Thr Cys Leu
                405                 410                 415
Val Lys Gly Phe Tyr Pro Ser Asp Ile Ala Val Glu Trp Glu Ser Asn
        420                 425                 430
Gly Gln Pro Glu Asn Asn Tyr Lys Thr Thr Pro Pro Val Leu Asp Ser
                435                 440                 445
Asp Gly Ser Phe Phe Leu Tyr Ser Arg Leu Thr Val Asp Lys Ser Arg
        450                 455                 460
Trp Gln Glu Gly Asn Val Phe Ser Cys Ser Val Met His Glu Ala Leu
465                 470                 475                 480
His Asn His Tyr Thr Gln Lys Ser Leu Ser Leu Ser Leu Gly Lys Met
                485                 490                 495
Phe Trp Val Leu Val Val Val Gly Gly Val Leu Ala Cys Tyr Ser Leu
        500                 505                 510
Leu Val Thr Val Ala Phe Ile Ile Phe Trp Val Arg Ser Lys Arg Ser
        515                 520                 525
Arg Gly Gly His Ser Asp Tyr Met Asn Met Thr Pro Arg Arg Pro Gly
        530                 535                 540
Pro Thr Arg Lys His Tyr Gln Pro Tyr Ala Pro Pro Arg Asp Phe Ala
545                 550                 555                 560
Ala Tyr Arg Ser Gly Gly Gly Arg Val Lys Phe Ser Arg Ser Ala Asp
                565                 570                 575
Ala Pro Ala Tyr Gln Gln Gly Gln Asn Gln Leu Tyr Asn Glu Leu Asn
        580                 585                 590
Leu Gly Arg Arg Glu Glu Tyr Asp Val Leu Asp Lys Arg Arg Gly Arg
        595                 600                 605
Asp Pro Glu Met Gly Gly Lys Pro Arg Arg Lys Asn Pro Gln Glu Gly
        610                 615                 620
Leu Tyr Asn Glu Leu Gln Lys Asp Lys Met Ala Glu Ala Tyr Ser Glu
625                 630                 635                 640
Ile Gly Met Lys Gly Glu Arg Arg Arg Gly Lys Gly His Asp Gly Leu
                645                 650                 655
Tyr Gln Gly Leu Ser Thr Ala Thr Lys Asp Thr Tyr Asp Ala Leu His
        660                 665                 670
Met Gln Ala Leu Pro Pro Arg Leu Glu Gly Gly Gly Glu Gly Arg Gly
        675                 680                 685
Ser Leu Leu Thr Cys Gly Asp Val Glu Glu Asn Pro Gly Pro Arg Met
        690                 695                 700
Leu Leu Leu Val Thr Ser Leu Leu Leu Cys Glu Leu Pro His Pro Ala
705                 710                 715                 720
Phe Leu Leu Ile Pro Arg Lys Val Cys Asn Gly Ile Gly Ile Gly Glu
                725                 730                 735
Phe Lys Asp Ser Leu Ser Ile Asn Ala Thr Asn Ile Lys His Phe Lys
        740                 745                 750
Asn Cys Thr Ser Ile Ser Gly Asp Leu His Ile Leu Pro Val Ala Phe
        755                 760                 765
Arg Gly Asp Ser Phe Thr His Thr Pro Pro Leu Asp Pro Gln Glu Leu
        770                 775                 780
```

```
Asp Ile Leu Lys Thr Val Lys Glu Ile Thr Gly Phe Leu Leu Ile Gln
785                 790                 795                 800

Ala Trp Pro Glu Asn Arg Thr Asp Leu His Ala Phe Glu Asn Leu Glu
                805                 810                 815

Ile Ile Arg Gly Arg Thr Lys Gln His Gly Gln Phe Ser Leu Ala Val
            820                 825                 830

Val Ser Leu Asn Ile Thr Ser Leu Gly Leu Arg Ser Leu Lys Glu Ile
        835                 840                 845

Ser Asp Gly Asp Val Ile Ile Ser Gly Asn Lys Asn Leu Cys Tyr Ala
    850                 855                 860

Asn Thr Ile Asn Trp Lys Lys Leu Phe Gly Thr Ser Gly Gln Lys Thr
865                 870                 875                 880

Lys Ile Ile Ser Asn Arg Gly Glu Asn Ser Cys Lys Ala Thr Gly Gln
                885                 890                 895

Val Cys His Ala Leu Cys Ser Pro Glu Gly Cys Trp Gly Pro Glu Pro
            900                 905                 910

Arg Asp Cys Val Ser Cys Arg Asn Val Ser Arg Gly Arg Glu Cys Val
        915                 920                 925

Asp Lys Cys Asn Leu Leu Glu Gly Glu Pro Arg Glu Phe Val Glu Asn
    930                 935                 940

Ser Glu Cys Ile Gln Cys His Pro Glu Cys Leu Pro Gln Ala Met Asn
945                 950                 955                 960

Ile Thr Cys Thr Gly Arg Gly Pro Asp Asn Cys Ile Gln Cys Ala His
                965                 970                 975

Tyr Ile Asp Gly Pro His Cys Val Lys Thr Cys Pro Ala Gly Val Met
            980                 985                 990

Gly Glu Asn Asn Thr Leu Val Trp Lys Tyr Ala Asp Ala Gly His Val
        995                 1000                1005

Cys His Leu Cys His Pro Asn Cys Thr Tyr Gly Cys Thr Gly Pro
    1010                1015                1020

Gly Leu Glu Gly Cys Pro Thr Asn Gly Pro Lys Ile Pro Ser Ile
    1025                1030                1035

Ala Thr Gly Met Val Gly Ala Leu Leu Leu Leu Leu Val Val Ala
    1040                1045                1050

Leu Gly Ile Gly Leu Phe Met
    1055                1060

<210> SEQ ID NO 39
<211> LENGTH: 679
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60
```

```
Lys Gly Leu Glu Trp Ile Gly Glu Ile Asn Pro Asp Ser Ser Thr Ile
 65                  70                  75                  80

Asn Tyr Ala Pro Ser Leu Lys Asp Lys Phe Ile Ile Ser Arg Asp Asn
                 85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Glu Ser Lys Tyr Gly Pro
            260                 265                 270

Pro Cys Pro Pro Cys Pro Ala Pro Glu Phe Glu Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Gln Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Gly Leu Pro Ser Ser Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Arg Leu Thr Val Asp Lys Ser Arg
    450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Met
```

```
                485                 490                 495
Phe Trp Val Leu Val Val Gly Gly Val Leu Ala Cys Tyr Ser Leu
            500                 505                 510
Leu Val Thr Val Ala Phe Ile Ile Phe Trp Val Arg Ser Lys Arg Ser
            515                 520                 525
Arg Gly Gly His Ser Asp Tyr Met Asn Met Thr Pro Arg Arg Pro Gly
        530                 535                 540
Pro Thr Arg Lys His Tyr Gln Pro Tyr Ala Pro Pro Arg Asp Phe Ala
545                 550                 555                 560
Ala Tyr Arg Ser Gly Gly Arg Val Lys Phe Ser Arg Ser Ala Asp
                565                 570                 575
Ala Pro Ala Tyr Gln Gln Gly Gln Asn Gln Leu Tyr Asn Glu Leu Asn
            580                 585                 590
Leu Gly Arg Arg Glu Glu Tyr Asp Val Leu Asp Lys Arg Arg Gly Arg
            595                 600                 605
Asp Pro Glu Met Gly Gly Lys Pro Arg Arg Lys Asn Pro Gln Glu Gly
        610                 615                 620
Leu Tyr Asn Glu Leu Gln Lys Asp Lys Met Ala Glu Ala Tyr Ser Glu
625                 630                 635                 640
Ile Gly Met Lys Gly Glu Arg Arg Arg Gly Lys Gly His Asp Gly Leu
                645                 650                 655
Tyr Gln Gly Leu Ser Thr Ala Thr Lys Asp Thr Tyr Asp Ala Leu His
            660                 665                 670
Met Gln Ala Leu Pro Pro Arg
        675

<210> SEQ ID NO 40
<211> LENGTH: 657
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asp Phe Ser Arg Tyr
            20                  25                  30
Trp Met Ser Trp Val Arg Gln Ala Pro Gly Lys Gly Leu Glu Trp Ile
        35                  40                  45
Gly Glu Ile Asn Pro Asp Ser Ser Thr Ile Asn Tyr Ala Pro Ser Leu
    50                  55                  60
Lys Asp Lys Phe Ile Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Pro Asp Gly Asn Tyr Trp Tyr Phe Asp Val Trp Gly Gln Gly
            100                 105                 110
Thr Leu Val Thr Val Ser Ser Gly Ser Thr Ser Gly Gly Gly Ser Gly
        115                 120                 125
Gly Gly Ser Gly Gly Gly Gly Ser Ser Asp Ile Gln Met Thr Gln Ser
    130                 135                 140
Pro Ser Ser Leu Ser Ala Ser Val Gly Asp Arg Val Thr Ile Thr Cys
145                 150                 155                 160
```

-continued

```
Lys Ala Ser Gln Asp Val Gly Ile Ala Val Ala Trp Tyr Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240

Val Glu Ile Lys Glu Ser Lys Tyr Gly Pro Pro Cys Pro Pro Cys Pro
            245                 250                 255

Ala Pro Glu Phe Glu Gly Gly Pro Ser Val Phe Leu Phe Pro Pro Lys
        260                 265                 270

Pro Lys Asp Thr Leu Met Ile Ser Arg Thr Pro Glu Val Thr Cys Val
    275                 280                 285

Val Val Asp Val Ser Gln Glu Asp Pro Glu Val Gln Phe Asn Trp Tyr
290                 295                 300

Val Asp Gly Val Glu Val His Asn Ala Lys Thr Lys Pro Arg Glu Glu
305                 310                 315                 320

Gln Phe Gln Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
        340                 345                 350

Gly Leu Pro Ser Ser Ile Glu Lys Thr Ile Ser Lys Ala Lys Gly Gln
    355                 360                 365

Pro Arg Glu Pro Gln Val Tyr Thr Leu Pro Pro Ser Gln Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
        420                 425                 430

Tyr Ser Arg Leu Thr Val Asp Lys Ser Arg Trp Gln Glu Gly Asn Val
    435                 440                 445

Phe Ser Cys Ser Val Met His Glu Ala Leu His Asn His Tyr Thr Gln
450                 455                 460

Lys Ser Leu Ser Leu Ser Leu Gly Lys Met Phe Trp Val Leu Val Val
465                 470                 475                 480

Val Gly Gly Val Leu Ala Cys Tyr Ser Leu Leu Val Thr Val Ala Phe
            485                 490                 495

Ile Ile Phe Trp Val Arg Ser Lys Arg Ser Arg Gly Gly His Ser Asp
        500                 505                 510

Tyr Met Asn Met Thr Pro Arg Arg Pro Gly Pro Thr Arg Lys His Tyr
    515                 520                 525

Gln Pro Tyr Ala Pro Pro Arg Asp Phe Ala Ala Tyr Arg Ser Gly Gly
    530                 535                 540

Gly Arg Val Lys Phe Ser Arg Ser Ala Asp Ala Pro Ala Tyr Gln Gln
545                 550                 555                 560

Gly Gln Asn Gln Leu Tyr Asn Glu Leu Asn Leu Gly Arg Arg Glu Glu
            565                 570                 575
```

```
Tyr Asp Val Leu Asp Lys Arg Arg Gly Arg Asp Pro Glu Met Gly Gly
                580                 585                 590

Lys Pro Arg Arg Lys Asn Pro Gln Glu Gly Leu Tyr Asn Glu Leu Gln
            595                 600                 605

Lys Asp Lys Met Ala Glu Ala Tyr Ser Glu Ile Gly Met Lys Gly Glu
        610                 615                 620

Arg Arg Arg Gly Lys Gly His Asp Gly Leu Tyr Gln Gly Leu Ser Thr
625                 630                 635                 640

Ala Thr Lys Asp Thr Tyr Asp Ala Leu His Met Gln Ala Leu Pro Pro
                645                 650                 655

Arg

<210> SEQ ID NO 41
<211> LENGTH: 836
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Gly Gly Ser Ser Gly
            260                 265                 270
```

```
Gly Gly Ser Gly Met Ala Leu Ile Val Leu Gly Gly Val Ala Gly Leu
            275                 280                 285

Leu Leu Phe Ile Gly Leu Gly Ile Phe Phe Lys Arg Gly Arg Lys Lys
        290                 295                 300

Leu Leu Tyr Ile Phe Lys Gln Pro Phe Met Arg Pro Val Gln Thr Thr
305                 310                 315                 320

Gln Glu Glu Asp Gly Cys Ser Cys Arg Phe Pro Glu Glu Glu Glu Gly
                325                 330                 335

Gly Cys Glu Leu Gly Gly Gly Arg Val Lys Phe Ser Arg Ser Ala Asp
                340                 345                 350

Ala Pro Ala Tyr Gln Gln Gly Gln Asn Gln Leu Tyr Asn Glu Leu Asn
            355                 360                 365

Leu Gly Arg Arg Glu Glu Tyr Asp Val Leu Asp Lys Arg Arg Gly Arg
        370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg Leu Glu Gly Gly Gly Glu Gly Arg Gly
        450                 455                 460

Ser Leu Leu Thr Cys Gly Asp Val Glu Glu Asn Pro Gly Pro Arg Met
465                 470                 475                 480

Leu Leu Leu Val Thr Ser Leu Leu Leu Cys Glu Leu Pro His Pro Ala
                485                 490                 495

Phe Leu Leu Ile Pro Arg Lys Val Cys Asn Gly Ile Gly Ile Gly Glu
            500                 505                 510

Phe Lys Asp Ser Leu Ser Ile Asn Ala Thr Asn Ile Lys His Phe Lys
        515                 520                 525

Asn Cys Thr Ser Ile Ser Gly Asp Leu His Ile Leu Pro Val Ala Phe
        530                 535                 540

Arg Gly Asp Ser Phe Thr His Thr Pro Pro Leu Asp Pro Gln Glu Leu
545                 550                 555                 560

Asp Ile Leu Lys Thr Val Lys Glu Ile Thr Gly Phe Leu Leu Ile Gln
                565                 570                 575

Ala Trp Pro Glu Asn Arg Thr Asp Leu His Ala Phe Glu Asn Leu Glu
            580                 585                 590

Ile Ile Arg Gly Arg Thr Lys Gln His Gly Gln Phe Ser Leu Ala Val
        595                 600                 605

Val Ser Leu Asn Ile Thr Ser Leu Gly Leu Arg Ser Leu Lys Glu Ile
        610                 615                 620

Ser Asp Gly Asp Val Ile Ile Ser Gly Asn Lys Asn Leu Cys Tyr Ala
625                 630                 635                 640

Asn Thr Ile Asn Trp Lys Lys Leu Phe Gly Thr Ser Gly Gln Lys Thr
                645                 650                 655

Lys Ile Ile Ser Asn Arg Gly Glu Asn Ser Cys Lys Ala Thr Gly Gln
            660                 665                 670

Val Cys His Ala Leu Cys Ser Pro Glu Gly Cys Trp Gly Pro Glu Pro
        675                 680                 685
```

Arg Asp Cys Val Ser Cys Arg Asn Val Ser Arg Gly Arg Glu Cys Val
690                 695                 700

Asp Lys Cys Asn Leu Leu Glu Gly Glu Pro Arg Glu Phe Val Glu Asn
705                 710                 715                 720

Ser Glu Cys Ile Gln Cys His Pro Glu Cys Leu Pro Gln Ala Met Asn
            725                 730                 735

Ile Thr Cys Thr Gly Arg Gly Pro Asp Asn Cys Ile Gln Cys Ala His
            740                 745                 750

Tyr Ile Asp Gly Pro His Cys Val Lys Thr Cys Pro Ala Gly Val Met
            755                 760                 765

Gly Glu Asn Asn Thr Leu Val Trp Lys Tyr Ala Asp Ala Gly His Val
770                 775                 780

Cys His Leu Cys His Pro Asn Cys Thr Tyr Gly Cys Thr Gly Pro Gly
785                 790                 795                 800

Leu Glu Gly Cys Pro Thr Asn Gly Pro Lys Ile Pro Ser Ile Ala Thr
                805                 810                 815

Gly Met Val Gly Ala Leu Leu Leu Leu Val Val Ala Leu Gly Ile
            820                 825                 830

Gly Leu Phe Met
        835

<210> SEQ ID NO 42
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr

```
                195                 200                 205
Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Gly Gly Ser Ser Gly
                260                 265                 270

Gly Gly Ser Gly Met Ala Leu Ile Val Leu Gly Gly Val Ala Gly Leu
                275                 280                 285

Leu Leu Phe Ile Gly Leu Gly Ile Phe Phe Lys Arg Gly Arg Lys Lys
    290                 295                 300

Leu Leu Tyr Ile Phe Lys Gln Pro Phe Met Arg Pro Val Gln Thr Thr
305                 310                 315                 320

Gln Glu Glu Asp Gly Cys Ser Cys Arg Phe Pro Glu Glu Glu Glu Gly
                325                 330                 335

Gly Cys Glu Leu Gly Gly Gly Arg Val Lys Phe Ser Arg Ser Ala Asp
                340                 345                 350

Ala Pro Ala Tyr Gln Gln Gly Gln Asn Gln Leu Tyr Asn Glu Leu Asn
                355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
                420                 425                 430

Tyr Gln Gly Leu Ser Thr Ala Thr Lys Asp Thr Tyr Asp Ala Leu His
                435                 440                 445

Met Gln Ala Leu Pro Pro Arg
    450                 455

<210> SEQ ID NO 43
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Ala Pro Ser Leu
        50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Ser Gly
        115                 120                 125

Gly Gly Ser Gly Gly Gly Ser Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
210                 215                 220

Cys Gln Gln Tyr Ser Ser Tyr Pro Tyr Thr Phe Gly Gln Gly Thr Lys
225                 230                 235                 240

Val Glu Ile Lys Gly Gly Gly Ser Ser Gly Gly Ser Gly Met Ala
                245                 250                 255

Leu Ile Val Leu Gly Gly Val Ala Gly Leu Leu Phe Ile Gly Leu
            260                 265                 270

Gly Ile Phe Phe Lys Arg Gly Arg Lys Lys Leu Leu Tyr Ile Phe Lys
        275                 280                 285

Gln Pro Phe Met Arg Pro Val Gln Thr Thr Gln Glu Glu Asp Gly Cys
290                 295                 300

Ser Cys Arg Phe Pro Glu Glu Glu Gly Gly Cys Glu Leu Gly Gly
305                 310                 315                 320

Gly Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
        355                 360                 365

Lys Pro Arg Arg Lys Asn Pro Gln Glu Gly Leu Tyr Asn Glu Leu Gln
370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 44
<211> LENGTH: 841
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Met Leu Leu Leu Val Thr Ser Leu Leu Leu Cys Glu Leu Pro His Pro

```
1               5                   10                  15
Ala Phe Leu Leu Ile Pro Glu Val Gln Leu Val Glu Ser Gly Gly Gly
                 20                  25                  30

Leu Val Gln Pro Gly Gly Ser Leu Arg Leu Ser Cys Ala Ala Ser Gly
                 35                  40                  45

Phe Asp Phe Ser Arg Tyr Trp Met Ser Trp Val Arg Gln Ala Pro Gly
                 50                  55                  60

Lys Gly Leu Glu Trp Ile Gly Glu Ile Asn Pro Asp Ser Ser Thr Ile
 65                  70                  75                  80

Asn Tyr Ala Pro Ser Leu Lys Asp Lys Phe Ile Ile Ser Arg Asp Asn
                 85                  90                  95

Ala Lys Asn Ser Leu Tyr Leu Gln Met Asn Ser Leu Arg Ala Glu Asp
                100                 105                 110

Thr Ala Val Tyr Tyr Cys Ala Arg Pro Asp Gly Asn Tyr Trp Tyr Phe
                115                 120                 125

Asp Val Trp Gly Gln Gly Thr Leu Val Thr Val Ser Ser Gly Ser Thr
                130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
                180                 185                 190

Ala Trp Tyr Gln Gln Lys Pro Gly Lys Val Pro Lys Leu Leu Ile Tyr
                195                 200                 205

Trp Ala Ser Thr Arg His Thr Gly Val Pro Asp Arg Phe Ser Gly Ser
                210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Gly Gly Gly Ser Ser Gly
                260                 265                 270

Gly Gly Ser Gly Met Phe Trp Val Leu Val Val Val Gly Gly Val Leu
                275                 280                 285

Ala Cys Tyr Ser Leu Leu Val Thr Val Ala Phe Ile Ile Phe Trp Val
                290                 295                 300

Arg Ser Lys Arg Ser Arg Gly Gly His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Gly Gly Arg Val Lys Phe
                340                 345                 350

Ser Arg Ser Ala Asp Ala Pro Ala Tyr Gln Gln Gly Gln Asn Gln Leu
                355                 360                 365

Tyr Asn Glu Leu Asn Leu Gly Arg Arg Glu Glu Tyr Asp Val Leu Asp
                370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
                420                 425                 430
```

```
Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg Leu Glu Gly Gly
    450                 455                 460

Gly Glu Gly Arg Gly Ser Leu Leu Thr Cys Gly Asp Val Glu Asn
465                 470                 475                 480

Pro Gly Pro Arg Met Leu Leu Leu Val Thr Ser Leu Leu Cys Glu
                    485                 490                 495

Leu Pro His Pro Ala Phe Leu Leu Ile Pro Arg Lys Val Cys Asn Gly
            500                 505                 510

Ile Gly Ile Gly Glu Phe Lys Asp Ser Leu Ser Ile Asn Ala Thr Asn
        515                 520                 525

Ile Lys His Phe Lys Asn Cys Thr Ser Ile Ser Gly Asp Leu His Ile
        530                 535                 540

Leu Pro Val Ala Phe Arg Gly Asp Ser Phe Thr His Thr Pro Pro Leu
545                 550                 555                 560

Asp Pro Gln Glu Leu Asp Ile Leu Lys Thr Val Lys Glu Ile Thr Gly
                565                 570                 575

Phe Leu Leu Ile Gln Ala Trp Pro Glu Asn Arg Thr Asp Leu His Ala
            580                 585                 590

Phe Glu Asn Leu Glu Ile Ile Arg Gly Arg Thr Lys Gln His Gly Gln
            595                 600                 605

Phe Ser Leu Ala Val Val Ser Leu Asn Ile Thr Ser Leu Gly Leu Arg
            610                 615                 620

Ser Leu Lys Glu Ile Ser Asp Gly Asp Val Ile Ile Ser Gly Asn Lys
625                 630                 635                 640

Asn Leu Cys Tyr Ala Asn Thr Ile Asn Trp Lys Lys Leu Phe Gly Thr
                645                 650                 655

Ser Gly Gln Lys Thr Lys Ile Ile Ser Asn Arg Gly Glu Asn Ser Cys
                660                 665                 670

Lys Ala Thr Gly Gln Val Cys His Ala Leu Cys Ser Pro Glu Gly Cys
            675                 680                 685

Trp Gly Pro Glu Pro Arg Asp Cys Val Ser Cys Arg Asn Val Ser Arg
            690                 695                 700

Gly Arg Glu Cys Val Asp Lys Cys Asn Leu Leu Glu Gly Glu Pro Arg
705                 710                 715                 720

Glu Phe Val Glu Asn Ser Glu Cys Ile Gln Cys His Pro Glu Cys Leu
                725                 730                 735

Pro Gln Ala Met Asn Ile Thr Cys Thr Gly Arg Gly Pro Asp Asn Cys
            740                 745                 750

Ile Gln Cys Ala His Tyr Ile Asp Gly Pro His Cys Val Lys Thr Cys
        755                 760                 765

Pro Ala Gly Val Met Gly Glu Asn Asn Thr Leu Val Trp Lys Tyr Ala
770                 775                 780

Asp Ala Gly His Val Cys His Leu Cys His Pro Asn Cys Thr Tyr Gly
785                 790                 795                 800

Cys Thr Gly Pro Gly Leu Glu Gly Cys Pro Thr Asn Gly Pro Lys Ile
                805                 810                 815

Pro Ser Ile Ala Thr Gly Met Val Gly Ala Leu Leu Leu Leu Leu Val
            820                 825                 830

Val Ala Leu Gly Ile Gly Leu Phe Met
            835                 840
```

<210> SEQ ID NO 45
<211> LENGTH: 460
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Gly Gly Gly Ser Ser Gly
            260                 265                 270

Gly Gly Ser Gly Met Phe Trp Val Leu Val Val Val Gly Gly Val Leu
        275                 280                 285

Ala Cys Tyr Ser Leu Leu Val Thr Val Ala Phe Ile Ile Phe Trp Val
    290                 295                 300

Arg Ser Lys Arg Ser Arg Gly Gly His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Gly Gly Gly Arg Val Lys Phe
            340                 345                 350

Ser Arg Ser Ala Asp Ala Pro Ala Tyr Gln Gln Gly Gln Asn Gln Leu
```

```
                355                 360                 365

Tyr Asn Glu Leu Asn Leu Gly Arg Arg Glu Tyr Asp Val Leu Asp
    370                 375                 380

Lys Arg Arg Gly Arg Asp Pro Glu Met Gly Gly Lys Pro Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Gly Lys
                420                 425                 430

Gly His Asp Gly Leu Tyr Gln Gly Leu Ser Thr Ala Thr Lys Asp Thr
            435                 440                 445

Tyr Asp Ala Leu His Met Gln Ala Leu Pro Pro Arg
450                 455                 460

<210> SEQ ID NO 46
<211> LENGTH: 438
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240

Val Glu Ile Lys Gly Gly Gly Ser Gly Gly Gly Ser Gly Met Phe
                245                 250                 255
```

-continued

```
Trp Val Leu Val Val Val Gly Gly Val Leu Ala Cys Tyr Ser Leu Leu
            260                 265                 270

Val Thr Val Ala Phe Ile Ile Phe Trp Val Arg Ser Lys Arg Ser Arg
            275                 280                 285

Gly Gly His Ser Asp Tyr Met Asn Met Thr Pro Arg Arg Pro Gly Pro
            290                 295                 300

Thr Arg Lys His Tyr Gln Pro Tyr Ala Pro Pro Arg Asp Phe Ala Ala
305                 310                 315                 320

Tyr Arg Ser Gly Gly Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Arg Gly Arg Asp
            355                 360                 365

Pro Glu Met Gly Gly Lys Pro Arg Arg Lys Asn Pro Gln Glu Gly Leu
    370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
                420                 425                 430

Gln Ala Leu Pro Pro Arg
            435
```

CS1 TARGETED CHIMERIC ANTIGEN RECEPTOR-MODIFIED T CELLS FOR TREATMENT OF AL AMYLOIDOSIS

CROSS-REFERENCE TO RELATED APPLICATIONS

This application is the 35 U.S.C. § 371 National Stage Application of International Application No. PCT/US2018/023381, filed Mar. 20, 2018, which claims priority to U.S. Provisional Application No. 62/473,980, filed Mar. 20, 2017. The entire contents of each of these applications is hereby incorporated herein by reference.

SEQUENCE LISTING

The instant application contains a Sequence Listing which has been submitted electronically in ASCII format and is hereby incorporated by reference in its entirety. Said ASCII copy, created on Jan. 2, 2020 is named SequenceListing.txt and is 129093 bytes in size.

BACKGROUND

Light chain amyloidosis (AL amyloidosis) is characterized by a clonal population of plasma cells in the bone marrow that produce monoclonal, light chains of kappa or lambda restriction. Amyloidgenic light chains fold improperly, thereby forming beta pleated sheets which combine to form fibrils. These amyloid fibrils deposit into tissues and organs including the heart, kidneys and peripheral nerves, where they progressively interfere with structure and function (Falk et al. 1997 N Engl J Med 337: 898-909). Without treatment, the prognosis is poor with a median survival of only 8 months (Kyle et al. 1997 N Engl J Med 336:1202-120). Treatment for AL amyloidosis is focused primarily on targeting the underlying plasma cell clone to arrest amyloid fibril production and allow for organ recovery. Options for treatment include chemotherapy regimens adopted from those used to treat multiple myeloma as well as high dose melphalan followed by autologous stem cell transplantation. Although patients with AL amyloidosis have benefited from the multitude of advances made for the treatment of plasma cell diseases in general, treatment is complicated by the frail nature of the population due to amyloid related organ dysfunction and the need to obtain a rapid, deep response to prevent a residual clone from causing further fibril deposition. Although long term remissions are possible with both stem cell transplantation and newer agents including proteosome inhibitors and immunomodulatory drugs, new well tolerated and effective treatments are needed.

SUMMARY

Described herein are methods for treating AL amyloidosis using chimeric antigen receptors (CARs) targeted to CS1, a cell surface glycoprotein that is a member of the signaling lymphocyte activation molecule (SLAM) receptor family. Described below are the results of studies evaluating bone marrow specimens from patients with plasma cell diseases. The patients had full clinical evaluations for a diagnosis of either multiple myeloma (MM) or AL amyloidosis, including characterization of the hematologic clone as well as organ involvement. Multi-color flow cytometry analysis was used to differentiate between malignant and normal plasma cells by analysis of aberrant ratios of intracellular kappa/lambda chains. A highly skewed kappa and lambda ratio is a reliable indicator of malignant clone of AL amyloidosis. Clonal populations of plasma cells were then evaluated for expression of B Cell Maturation Antigen (BCMA) and CS1 expression. These studies demonstrated that CS1 is expressed on the clonal plasma cells of patients with AL amyloidosis and that BCMA is not significantly expressed on the plasma cells in AL amyloidosis patients. This is in contrast to MM, where BCMA is thought to be ubiquitously expressed. Additional studies described below show that a CS1-targeted CAR can effectively eliminate CS1-expressing cells in a murine model.

Described herein is a method for treating light chain amyloidosis comprising administering to a patient in need thereof a population of human T cells transduced by a vector comprising an expression cassette encoding a chimeric antigen receptor, wherein chimeric antigen receptor comprises: a CS1 scFv; a spacer region; a transmembrane domain; a co-signaling domain; and CD3 ζ signaling domain.

In various embodiments: chimeric antigen receptor comprises: a CS1 scFv; a spacer region; a CD28 transmembrane domain; a CD28 co-signaling domain; and a CD3 ζ signaling domain; the chimeric antigen receptor comprises: a CS1 scFv; a spacer region; a CD4 transmembrane domain; a 4-1BB co-signaling domain; and a CD3 ζ signaling domain; the chimeric antigen receptor comprises: a CS1 scFv; a spacer region comprising an amino acid sequence selected from SEQ ID Nos:2-5 and 9-12; a CD4 transmembrane domain; a 4-1BB co-signaling domain; and a CD3 ζ signaling domain; the chimeric antigen receptor comprises: a CS1 scFv; a spacer region comprising an amino acid sequence selected from SEQ ID Nos:2-5 and 9-12; a CD28 transmembrane domain; a CD28 co-signaling domain; and a CD3 ζ signaling domain; the chimeric antigen receptor comprises: a CS1 scFv; a spacer a spacer comprising an amino acid sequence selected from SEQ ID Nos:2-5 and 9-12; CD4 transmembrane domain; a 4-1BB co-signaling domain; and CD3 ζ signaling domain; the chimeric antigen receptor comprises: a spacer a spacer comprising an amino acid sequence selected from SEQ ID Nos:2-5 and 9-12; a CD28 transmembrane domain; a CD28 co-signaling domain; and a CD3 ζ signaling domain; the chimeric antigen receptor comprises an amino acid sequence at least 95% identical to an amino acid sequence selected from: SEQ ID NOs: 30, 31, 33, 34, 36, 37, 39, 40, 42, 43, 44 and 45; the chimeric antigen receptor comprises an amino acid sequence identical to an amino acid sequence selected from: SEQ ID NOs: 30, 31, 33, 34, 36, 37, 39, 40, 42, 43, 44 and 45; the chimeric antigen receptor comprises an amino acid sequence identical to an amino acid sequence selected from: SEQ ID NOs: 30, 31, 33, 34, 36, 37, 39, 40, 42, 43, 44 and 45, each with no more than 5 single amino acid substitutions; at least 20%, 30%, or 40% of the transduced human T cells are central memory T cells; at least 30% of the transduced human T cells are CD4+ and CD62L+ or CD8+ and CD62L+; the population of human T cells are autologous to the patient; and the population of human T cells are allogenic to the patient.

FIG. 2A-D depicts the results of studies using a CS1-targeted CART cells showing that they are cytotoxic against CS1 positive cells and induce durable tumor regression in mice. (A) Schematics of CS1 CAR constructs, each include an antigen-specific scFv, IgG4 hinge region, and a CD28 costimulatory domain as well as a CD3 ζ signaling domain. The IgG4 hinge region was shortened by deleting the CH2 portion. The CAR sequence is followed by a T2A ribosomal skip sequence and then the coding sequence for the EGFRt tracking/suicide gene. (B) Purified central memory T cells ($T_{CM}$) were activated and transduced with a lentiviral vector encoding the CS1 CAR. CAR expression was detected by staining the cells with antibody against EGFR cetuximab. (C) Cytotoxicity of the propagated CS1 CAR T cells was evaluated using 4-hour $^{51}$Cr release assays after co-culture with $^{51}$Cr-labeled CS1 positive target cells, MM.1S. OKT3 expressing LCLs were used as positive control and myeloid leukemia KG1A were used as negative control. Non-transduced mock T cells were negative effector cells. (D) 2×10$^6$ ffLucGFP MM.1S that were engineered to express luciferase (ffluc) and green florescence protein (GFP) cells were intratibially (i.t.) injected into NOD/Scid IL2RγCnull (NSG) mice. Five days following tumor inoculation, mice were injected i.v. with 1×10$^6$ CS1 CAR T cells and non-transduced mock cells were infused into control mice. Tumor signals were monitored with Xenogen imaging once a week.

Figure 3:
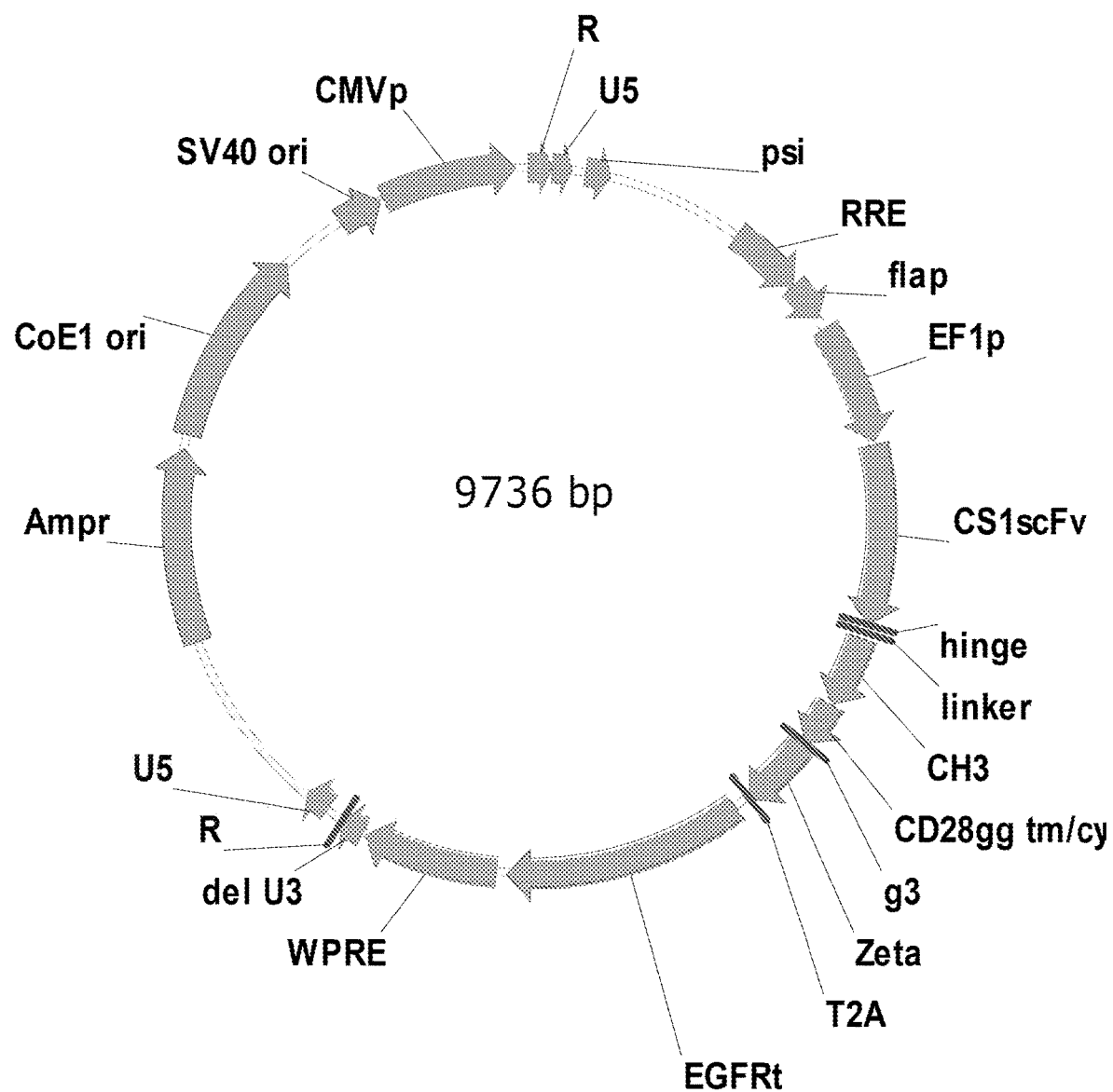

FIG. 3 is a schematic depiction of a CS1 CAR expressing lentiviral vector (CS1scFv-IgG4(HL-CH3)-CD28gg-Zeta (CO)-T2A-EGFRt_epHIV7). The CS1 CAR construct includes: a GMCSF signal sequence, CS1 scFv, IgG4 hinge region, linker, CH3 domain, a CD28 co-stimulatory domain and CD3ζ signaling domain. The CAR construct is followed by a T2A ribosomal skip sequence, and then suicide gene EGFRt coding sequence. The CAR and EGFRt molecules are expressed from a single transcript.

FIG. 4 depicts the amino acid sequence of a CS1 CAR that includes signal peptide, a ribosomal skip sequence and an EGFRt (SEQ ID NO:29).

FIG. 5 depicts the amino acid sequence of CS1scFv-IgG4 (HL-CH3)-CD4tm-41BB-Zeta-T2A-EGFRt (SEQ ID NO:32).

FIG. 6 depicts the amino acid sequence of CS1scFv-IgG4 (L235E, N297Q)-CD4tm-41BB-Zeta-T2A-EGFRt (SEQ ID NO:35).

FIG. 7 depicts the amino acid sequence of CS1scFv-IgG4 (L235E, N297Q)-CD28tm-CD28gg-Zeta-T2A-EGFRt (SEQ ID NO:38).

FIG. 8 depicts the amino acid sequence of CS1scFv-Linker-CD4tm-41BB-Zeta-T2A-EGFRt (SEQ ID NO:41).

FIG. 9 depicts the amino acid sequence of CS1scFv-Linker-CD28tm-CD28gg-Zeta-T2A-EGFRt (SEQ ID NO:44).

DETAILED DESCRIPTION

Example 1: CS1 and BCMA Expression in AL Amyloidosis and Multiple Myeloma

Fourteen patients with AL amyloidosis were studied. Analysis of CS1 and BCMA expression on neoplastic plasma cells from these patients reveal that the cells preferentially express CS1, but not BCMA. Briefly, bone marrow mononuclear cells were isolated from patients diagnosed with AL amyloidosis and labelled with antibodies against CS and BCMA followed by staining for kappa/lambda. An example of gating on the clonal population of plasma cells in a patient with kappa restricted disease followed by analysis of CS1 expression is shown in FIG. 1A. All of the AL amyloidosis samples expressed high levels of CS1 (76.5±4.7%) but were negative for or demonstrated very low expression of BCMA (4.9±0.8%) (FIG. 1B).

For comparison, bone marrow specimens from 10 patients MM were tested during the same time period using the same methodology (FIG. 1C). The clonal plasma cells of patients with MM express CS1 similarly to that seen in AL; however, BCMA is comparatively much more frequently expressed. Interestingly, the lack of expression of BCMA on the plasma cells in AL patients suggests that the clonal plasma cell in AL is unique compared to myeloma cells.

Example 2: Cell Killing by CS1-Targeted CAR

Figure 2:
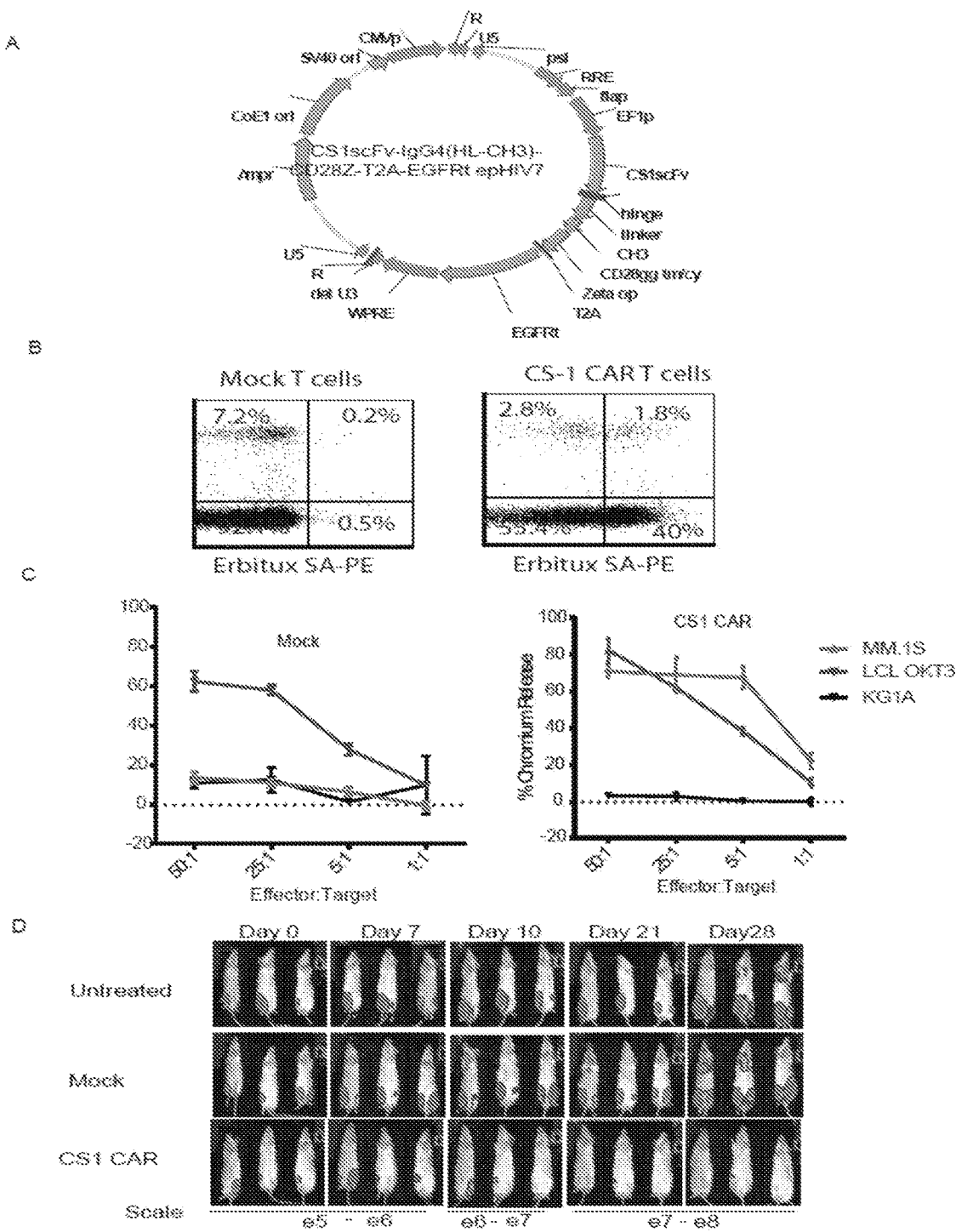

To explore the utility of CS1 as a target for CAR T cell therapy for AL amyloidosis, we tested a second generation CS1 CAR (FIG. 2A), containing a CD28gg costimulatory domain, the ribosomal-skip T2A sequence, and the truncated EGF receptor sequence (EGFRt) as a selection, tracking, and ablation molecule and incorporated into a SIN lentiviral vector, described in greater detail below. Purified central memory T cells ($T_{CM}$) were activated and transduced with a lentiviral vector encoding CS1 CAR and expanded in the presence of IL-2 50 U/ml and IL-15 0.5 ng/ml for 3 weeks. CAR expression was monitored by staining the cells with cetuximab-biotin and streptavidin (SA) (FIG. 2B). Cytotoxicity of the expanded CS1 CAR T cells was evaluated using 4-hour $^{51}$Cr release assays after co-culture with $^{51}$Cr-labeled CS1+ target cells (MM.1S) (FIG. 2C)

Six- to ten-week old NOD/Scid IL2RγCnull mice were injected intratibially (i.t.) injected with 2×106 ffLucGFP MM.1S that were engineered to express luciferase (ffluc) and green fluorescent protein (GFP). Five days following tumor inoculation, mice were injected intravenously (i.v.) with 1×10$^6$ CS1 CART cells, and non-transduced mock cells were infused into control mice. Anesthetized mice were imaged weekly using a Xenogen IVIS 100 series system (Xenogen, Alameda, Calif.). Photons from ffLuc+ tumor xenografts were quantified using the software program Living Image (Xenogen), and the bioluminescence signal was measured as total photon flux normalized for exposure time and surface area and expressed in units of photons per second per cm$^2$ per steradian.

To test the antitumor activity, MM.1S were inoculated into NSG mice by intra-tibial injection. Once the tumor engraftment was confirmed, 1×10$^6$ CS1 CAR T cells were infused into tumor-bearing mice intravenously. The CS1 CAR T cells exhibit specific and efficient killing of CS1 positive cells (MM.1S) (FIG. 2C). Anti-tumor studies in the animal model showed that CS1 CAR T cells induced significant tumor remission as compared to mock T cell treated mice (FIG. 2D).

These findings support for the use of CS1-directed CART cell therapy for patients with AL amyloidosis. AL is an ideal setting to explore CAR mediated therapy. The relative low number of malignant cells to be targeted presents an opportunity for successful eradication of the small but destructive clone as well as a minimal risk for complications related to cytokine release syndrome. Moreover, the relatively safe profile of the CS1-targeting antibody elotuzumab indicates that CS1 CAR T cells may likewise yield favorable outcomes in this regard. Our work represents a novel application of CS1-directed CAR T cells while revealing that, in contrast to preclinical experience with MM, BCMA would not be a suitable target. With our preclinical data showing efficacy of our CS1-directed CAR T cells, we plan to move forward with a clinical trial using CS1 CAR T cells for AL.

Example 3: CS1-Targeted CAR

CS1-targeted CAR suitable for use in treating AL amyloidosis include CAR which comprise an extracellular domain, a transmembrane domain and an intracellular signaling domain. The extracellular domain includes a CS1-specific scFv region or a variant thereof and a spacer, comprising, for example, a portion of human Fc domain. The extracellular domain enables the CAR, when expressed on the surface of a T cell, to direct T cell activity to cells expressing CS1. The transmembrane domain includes, for example, a CD4 transmembrane domain, a CD8 transmembrane domain, a CD28 transmembrane domain, or a CD3 transmembrane domain. The intracellular signaling domain includes the signaling domain from the zeta chain of the human CD3 complex (CD3ζ) and one or more costimulatory domains, for example, a 4-1BB costimulatory domain. The inclusion of a costimulatory domain, such as the 4-1BB (CD137) costimulatory domain in series with CD3ζ in the intracellular region enables the T cell to receive co-stimulatory signals. T cells, for example, patient-specific, autologous T cells can be engineered to express the CARs described herein, and the engineered cells can be expanded and used therapeutically. Various T cell subsets, including both alpha beta T cells and gamma delta T cells, can be used. In addition, the CAR can be expressed in other immune cells such as NK cells. Where a patient is treated with an immune cell expressing a CAR described herein the cell can be an autologous T cell or an allogenic T cell. In some instances, the cells used are a cell population that includes both CD4+ and CD8+ central memory T cells ($T_{CM}$), which are CD62L+, CCR7+, CD45RO+, and CD45RA−. The cell population can include other types of T cells as well. Several CS1-targeting CAR are described in detail in WO 2016/090369.

CS-1 Targeting scFv

The CS1-targeted CAR described herein include a CS1-targeting scFv (e.g., an scFv including the sequence: EVQLVESGGGLVQPGGSLRLS-CAASGFDFSRYWMSWVRQAPGKGLEWIGEINP DSSTINYAPSLKDKFIISRDNAKNSLYLQMNSLRAED-TAVYYCARPDGNYWYFD VWGQGTLVTVSSGST-SGGGSGGGSGGGGSSDIQMTQSPSSL-SASVGDRVTITCK ASQDVGIAVAWYQQKPGKVPKLLIYWAST-RHTGVPDRFSGSGSGTDFTLTISSLQ PED-VATYYCQQYSSYPYTFGQGTKVEIK; SEQ ID NO:1) or a variant thereof having 1-5 (e.g., 1 or 2) amino acid modifications (e.g., substitutions).

Useful CS1 CAR consist of or comprises the amino acid sequence of any of SEQ ID NOs:31, 34, 37, 40, 43, and 46 (mature CAR lacking a signal sequence) or the CS1 CAR consists of or comprises the amino acid sequence of any of SEQ ID NOs:30, 33, 36, 39, 42, and 45 (immature CAR having a GMCSFRa signal sequence). The CAR and can be expressed in a form that includes a signal sequence, e.g., a human GM-CSF receptor alpha signal sequence (MLLLVT-SLLLCELPHPAFLLIP; SEQ ID NO:26). The CAR can be expressed with additional sequences that are useful for monitoring expression, for example a T2A skip sequence and a truncated EGFRt. Thus, the CAR can comprise or consist of the amino acid sequence of any of SEQ ID Nos: 29-46 or can comprise or consist of an amino acid sequence that is at least 95%, 96%, 97%, 98% or 99% identical to any of SEQ ID Nos: 29-46. The CAR can comprise or consist of the amino acid sequence of any of SEQ ID Nos: 29-46 with up to 1, 2, 3, 4 or 5 amino acid changes (preferably conservative amino acid changes).

Spacer Region

The CAR described herein can include a spacer located between the CS1 targeting domain (i.e., a CS1 ScFv or variant thereof) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |
| IgG4 hinge(S → P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (S228P) + linker | 22 aa | ESKYGPPCPPCPGGGSSGGGSG (SEQ ID NO: 5) |
| CD28 hinge | 39 aa | IEVMYPPPYLDNEKSNGTIIHV KGKHLCPSPLFPGPSKP (SEQ ID NO: 6) |
| CD8 hinge-48aa | 48 aa | AKPTTTPAPRPPTPAPTIASQP LSLRPEACRPAAGGAVHTRGLD FACD (SEQ ID NO: 7) |
| CD8 hinge-45aa | 45 aa | TTTPAPRPPTPAPTIASQPLSL RPEACRPAAGGAVHTRGLDFAC D (SEQ ID NO: 8) |
| IgG4 (HL-CH3) (includes S228P in hinge) | 129 aa | ESKYGPPCPPCPGGGSSGGGSG GQPREPQVYTLPPSQEEMTKNQ VSLTCLVKGFYPSDIAVEWESN GQPENNYKTTPPVLDSDGSFFL YSRLTVDKSRWQEGNVFSCSVM HEALHNHYTQKSLSLSLGK (SEQ ID NO: 9) |
| IgG4 (L235E, N297Q) | 229 aa | ESKYGPPCPSCPAPEFEGGPSV FLFPPKPKDTLMISRTPEVTCV VVDVSQEDPEVQFNWYVDGVEV HQAKTKPREEQFQSTYRVVSVL TVLHQDWLNGKEYKCKVSNKGL PSSIEKTISKAKGQPREPQVYT LPPSQEEMTKNQVSLTCLVKGF YPSDIAVEWESNGQPENNYKTT PPVLDSDGSFFLYSRLTVDKSR WQEGNVFSCSVMHEALHNHYTQ KSLSLSLGK (SEQ ID NO: 10) |
| IgG4 (S228P, L235E, N297Q) | 229 aa | ESKYGPPCPPCPAPEFEGGPSV FLFPPKPKDTLMISRTPEVTCV VVDVSQEDPEVQFNWYVDGVEV HQAKTKPREEQFQSTYRVVSVL TVLHQDWLNGKEYKCKVSNKGL PSSIEKTISKAKGQPREPQVYT |

TABLE 1-continued

Examples of Spacers

| Name | Length | Sequence |
|---|---|---|
|  |  | LPPSQEEMTKNQVSLTCLVKGF YPSDIAVEWESNGQPENNYKTT PPVLDSDGSFFLYSRLTVDKSR WQEGNVFSCSVMHEALHNHYTQ KSLSLSLGK (SEQ ID NO: 11) |
| IgG4(CH3) | 107 aa | GQPREPQVYTLPPSQEEMTKNQ VSLTCLVKGFYPSDIAVEWESN GQPENNYKTTPPVLDSDGSFFL YSRLTVDKSRWQEGNVFSCSVM HEALHNHYTQKSLSLSLGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one ore more amino acid modifications, for example, 1, 2, 3, 4 or 5 substitutions, e.g., substitutions that reduce off-target binding.

The hinge/linker region can also comprise a IgG4 hinge region having the sequence ESKYGPPCPSCP (SEQ ID NO:4) or ESKYGPPCPPCP (SEQ ID NO:3).

The hinge/linger region can also comprise the sequence ESKYGPPCPPCP (SEQ ID NO:3) followed by the linker sequence GGGSSGGGSG (SEQ ID NO:2) followed by IgG4 CH3 sequence GQPREPQVYTLPP SQEEMTKNQVSLTCLVKGFYP SDIAVEWESNGQPENNYKTT PPVLDSDGSFFLY-SRLTVDKSRWQEGNVFSCSVMHEALHN-HYTQKSLSLSLGK (SEQ ID NO:12). Thus, the entire linker/spacer region can comprise the sequence: ESKY-GPPCPPCPGGGSSGGGSGGQPREPQVYTLPP SQEEMTKNQVSLTCLVKGFY PSDIAVEWESNGQPEN-NYKTTPPVLDSDGSFFLY-SRLTVDKSRWQEGNVFSCSV MHEALHN-HYTQKSLSLSLGK (SEQ ID NO:11). In some cases, the spacer has 1, 2, 3, 4, or 5 single amino acid changes (e.g., conservative changes) compared to SEQ ID NO:11. In some cases, the IgG4 Fc hinge/linker region that is mutated at two positions (L235E; N297Q) in a manner that reduces binding by Fc receptors (FcRs).

Transmembrane Domain

A variety of transmembrane domains can be used in the CARS. Table 2 includes examples of suitable transmembrane domains. Where a spacer region is present, the transmembrane domain is located carboxy terminal to the spacer region.

TABLE 2

Examples of Transmembrane Domains

| Name | Accession | Length | Sequence |
|---|---|---|---|
| CD3z | J04132.1 | 21 aa | LCYLLDGILFIYGVILTAL FL (SEQ ID NO: 13) |

TABLE 2-continued

Examples of Transmembrane Domains

| Name | Accession | Length | Sequence |
|---|---|---|---|
| CD28 | NM_006139 | 27 aa | FWVLVVVGGVLACYSLLVT VAFIIFWV (SEQ ID NO: 14) |
| CD28 (M) | NM_006139 | 28 aa | MFWVLVVVGGVLACYSLLV TVAFIIFWV (SEQ ID NO: 15) |
| CD4 | M35160 | 22 aa | MALIVLGGVAGLLLFIGLG IFF (SEQ ID NO: 16) |
| CD8tm | NM_001768 | 21 aa | IYIWAPLAGTCGVLLLSLV IT (SEQ ID NO: 17) |
| CD8tm2 | NM_001768 | 23 aa | IYIWAPLAGTCGVLLLSLV ITLY (SEQ ID NO: 18) |
| CD8tm3 | NM_001768 | 24 aa | IYIWAPLAGTCGVLLLSLV ITLYC (SEQ ID NO: 19) |
| 41BB | NM_001561 | 27 aa | IISFFLALTSTALLFLLFF LTLRFSVV (SEQ ID NO: 20) |

Costimulatory Domain

The costimulatory domain can be any domain that is suitable for use with a CD3 ζ signaling domain. In some cases, the costimulatory domain is a CD28 costimulatory domain that includes a sequence that is at least 90%, at least 95%, at least 98% identical to or identical to: RSKRSR GGHSDYMNMTPRRPGPTRKHYQPYAPPRDFAAYRS (SEQ ID NO:23; LL to GG amino acid change double underlined). In some cases, the CD28 co-signaling domain has 1, 2, 3, 4 of 5 amino acid changes (preferably conservative and preferably not in the underlined GG sequence) compared to SEQ ID NO:23. In some cases the co-signaling domain is a 4-1BB co-signaling domain that includes a sequence that is at least 90%, at least 95%, at least 98% identical to or identical to: KRGRKKLLY-IFKQPFMRPVQTTQEEDGCSCRFPEEEEGGCEL (SEQ ID NO:24). In some cases the 4-1BB co-signaling domain has 1, 2, 3, 4 of 5 amino acid changes (preferably conservative) compared to SEQ ID NO:24.

The costimulatory domain(s) are located between the transmembrane domain and the CD3ζ signaling domain. Table 3 includes examples of suitable costimulatory domains together with the sequence of the CD3ζ signaling domain.

TABLE 3

CD3ζ Domain and Examples of Costimulatory Domains

| Name | Accession | Length | Sequence |
|---|---|---|---|
| CD3ζ | J04132.1 | 113 aa | RVKFSRSADAPAYQQGQNQLYNELN LGRREEYDVLDKRRGRDPEMGGKPR RKNPQEGLYNELQKDKMAEAYSEIG MKGERRRGKGHDGLYQGLSTATKDT YDALHMQALPPR (SEQ ID NO: 21) |

TABLE 3-continued

CD3ζ Domain and Examples of Costimulatory Domains

| Name | Accession | Length | Sequence |
|------|-----------|--------|----------|
| CD28 | NM_006139 | 42 aa | RSKRSRLLHSDYMNMTPRRPGPTRK HYQPYAPPRDFAAYRS (SEQ ID NO: 22) |
| CD28gg* | NM_006139 | 42 aa | RSKRSRGGHSDYMNMTPRRPGPTRK HYQPYAPPRDFAAYRS (SEQ ID NO: 23) |
| 41BB | NM_001561 | 42 aa | KRGRKKLLYIFKQPFMRPVQTTQEE DGCSCRFPEEEEGGCEL (SEQ ID NO: 24) |
| OX40 | | 42 aa | ALYLLRRDQRLPPDAHKPPGGGSFR TPIQEEQADAHSTLAKI (SEQ ID NO: 25) |

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3ζ signaling domain and in some cases a short linker consisting of 2-10, e.g., 3 amino acids (e.g., GGG) is positioned between the costimulatory domain and the CD3ζ signaling domain.

CD3ζ Signaling Domain

The CD3ζ Signaling domain can be any domain that is suitable for use with a CD3ζ signaling domain. In some cases, the CD3ζ signaling domain includes a sequence that is at least 90%, at least 95%, at least 98% identical to or identical to:
RVKFSRSADAPAYQQGQNQLYNELNLGRREEY-DVLDKRRGRDPEMGGKPRRK NPQEGLYNELQKDK-MAEAYSEIGMKGERRRGKGHDGLYQGLSTATKDTY-DAL HMQALPPR (SEQ ID NO:21). In some cases, the CD3ζ signaling has 1, 2, 3, 4 of 5 amino acid changes (preferably conservative) compared to SEQ ID NO:21.

Truncated EGFR

The CD3ζ signaling domain can be followed by a ribosomal skip sequence (e.g., LEGGGEGRGSLLTCGD-VEENPGPR; SEQ ID NO:27) and a truncated EGFR having a sequence that is at least 90%, at least 95%, at least 98% identical to or identical to: LVTSLLLCELPHPAFLLIP-RKVCNGIGIGEFKDSLSINATNIKHFKNCTSISGDLHIL PVAFRGDSFTHTPPLDPQELDI-LKTVKEITGFLLIQAWPENRTDLHAFENLEIIRGR TKQHGQFSLAVVSLNITSLGLRSLKEISDGDVIIS-GNKNLCYANTINWKKLFGTSG QKTKIISNRGENSCK-ATGQVCHALCSPEGCWGPEPRDCVSCRNVSR-GRECVDKC NLLEGEPREFVENSECIQCHPECLPQAMNITCT-GRGPDNCIQCAHYIDGPHCVKT CPAGVM-GENNTLVWKYADAGHVCHLCHPNCTYGCTGPG-LEGCPTNGPKIPSIA TGMVGALLLLLVVALGIGLFM (SEQ ID NO:28). In some cases, the truncated EGFR has 1, 2, 3, 4 of 5 amino acid changes (preferably conservative) compared to SEQ ID NO:28.

A patient suffering from AL amyloidosis can be administered a population of human T cells transduced by a vector comprising an expression cassette encoding a CS1 chimeric antigen receptor described herein (e.g., a CAR that comprises or consists of the amino acid sequence of any of SEQ ID Nos: 29-46 or an amino acid sequence that is at least 95%, 96%, 97%, 98% or 99% identical to any of SEQ ID Nos: 29-46 or the amino acid sequence of any of SEQ ID Nos: 29-46 with up to 1, 2, 3, 4 or 5 amino acid changes (preferably conservative amino acid changes). In various embodiments: the population of human T cells are central memory T cells ($T_{CM}$), e.g., CD8+/CD4+ $T_{CM}$.

An amino acid modification refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

The CS1 CAR can include a sequence that is at least 90%, at least 95%, at least 98% identical to or identical to the amino acid sequence depicted in FIGS. 4-9 (SEQ ID Nos: 29-46, either including or excluding the GMCSFRa signal sequence and either including or excluding the T2A ribosomal skip sequence and the truncated EGFRt).

A variety of CS-1 targeting CAR are described in WO 2016/090369, and these CAR can be useful for treating AL amyloidosis.

Among the CAR targeting CS1 described herein are those summarized in Table 4 in which the spacer region, transmembrane domain and costimulatory domain(s) for each CAR are indicated.

TABLE 4

Examples of CAR Targeting CS1

| Name | SEQ ID NO* | FIG. | Spacer | TM | Costimulatory Domain(s) |
|---|---|---|---|---|---|
| CS1scFv-IgG4(HL-CH3)-CD28tm-CD28gg-Zeta-T2A-EGFRt. | 29//30//31 | 4 | IgG4(HL-CH3) | CD28 | CD28GG |
| CS1scFv-IgG4(HL-CH3)-CD4tm-41BB-Zeta-T2A-EGFRt. | 32//33//34 | 5 | IgG4(HL-CH3) | CD4 | 4-1BB |
| CS1scFv-IgG4(L235E, N297Q)-CD4tm-41BB-Zeta-T2A-EGFRt. | 35//36//37 | 6 | IgG4(L235E, N297Q) | CD4 | 4-1BB |
| CS1scFv-IgG4(L235E, N297Q)-CD28tm-CD28gg-Zeta-T2A-EGFRt | 38//39//40 | 7 | IgG4(L235E, N297Q) | CD28 | CD28GG |
| CS1scFv-Linker-CD4tm-41BB-Zeta-T2A-EGFRt. | 41//42//43 | 8 | L | CD4 | 4-1BB |
| CS1scFv-Linker-CD28tm-CD28gg-Zeta-T2A-EGFRt | 44//45//46 | 9 | L | CD28 | CD28GG |

*SEQ ID NOs for: entire sequence depicted including GMCSFRa signal sequence, T2A and EGFRt//sequence including GMCSFRa signal sequence but excluding T2A and EGFRt//sequence excluding GMCSFRa signal sequence, T2A and EGFRt.

In some cases, the CS1 CAR can be produced using a vector in which the CAR open reading frame is followed by a T2A ribosome skip sequence and a truncated EGFR (EGFRt), which lacks the cytoplasmic signaling tail. In this arrangement, co-expression of EGFRt provides an inert, non-immunogenic surface marker that allows for accurate measurement of gene modified cells, and enables positive selection of gene-modified cells, as well as efficient cell tracking of the therapeutic T cells in vivo following adoptive transfer. Efficiently controlling proliferation to avoid cytokine storm and off-target toxicity is an important hurdle for the success of T cell immunotherapy. The EGFRt incorporated in the CS1CAR lentiviral vector can act as suicide gene to ablate the CAR+ T cells in cases of treatment-related toxicity.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a lentiviral vector that directs the expression of an CS1 CAR as well as a non-immunogenic surface marker for in vivo detection, ablation, and potential ex vivo selection. The activated/genetically modified CS1 central memory T cells can be expanded in vitro with IL-2/IL-15 and then cryopreserved.

Example 4: Construction and Structure of epHIV7 Used for Expression of CS1-Specific CAR The pHIV7 plasmid is a parent plasmid from which the clinical vectors expressing a CS1 CAR can be derived. The epHIV7 vector used for expression of the CAR was produced from pHIV7 vector (Wang et al. 2011 Blood 118: 1255). Importantly, this vector uses the human EF1 promoter to drive expression of the CAR. Both the 5' and 3' sequences of the vector were derived from pv653RSN as previously derived from the HXBc2 provirus. The polypurine tract DNA flap sequences (cPPT) were derived from HIV-1 strain pNL4-3 from the NIH AIDS Reagent Repository.

Construction of pHIV7 was carried out as follows. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step 1, the sequences from 5' LTR to rev-responsive element (RRE) made p5'HIV-1 51, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to make pHIV-6. In Step 6, a 190-bp BglII-BamHI fragment containing the cPPT DNA flap sequence from HIV-1 pNL4-3 (55) was amplified from pNL4-3 and placed between the RRE and the WPRE sequences in pHIV6 to make pHIV-7. This parent plasmid pHIV7-GFP (GFP, green fluorescent protein) was used to package the parent vector using a four-plasmid system.

A packaging signal, psi w, is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector, are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The removed from this system. In addition, epHIV7 vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes. Table 5 summarizes the various regulator elements present in epHIV7.

Figure 1:
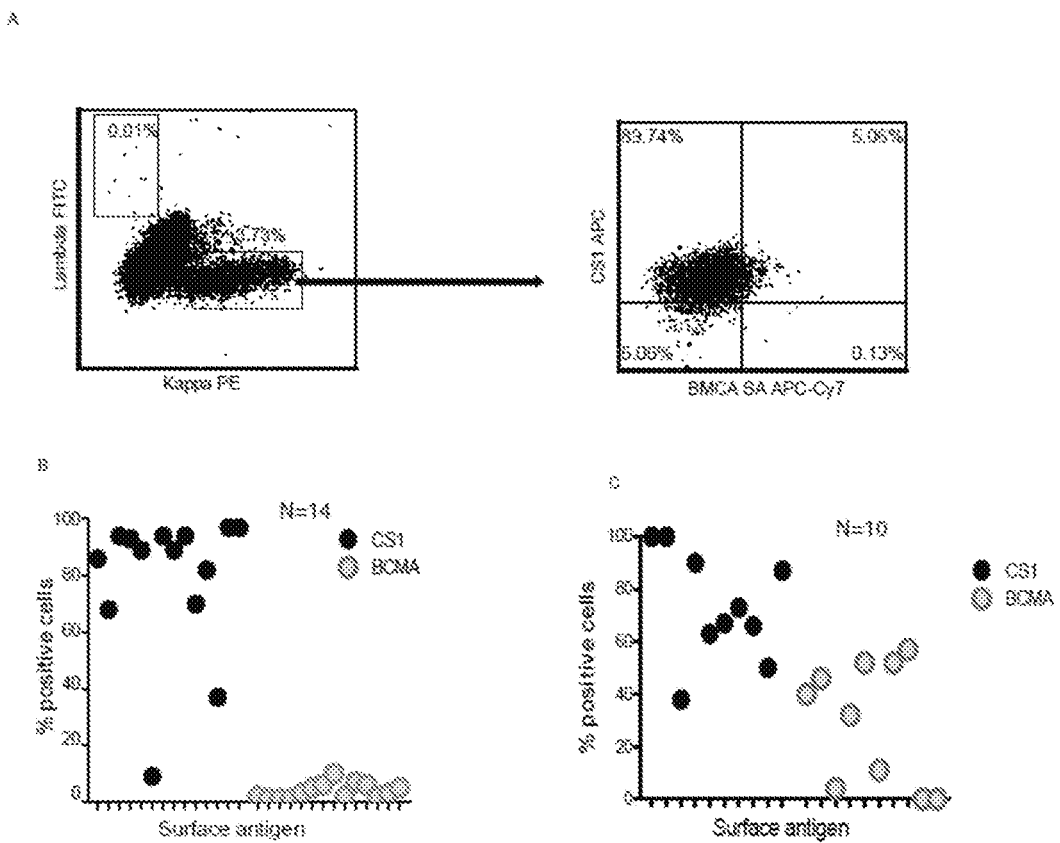
FIG. 1A-C depicts the results of studies showing that neoplastic plasma cell in AL amyloidosis preferentially express CS1. (A) Bone marrow mononuclear cells were isolated from patients with diagnosed AL amyloidosis and multiple myeloma and labeled with antibodies against CS1 and BCMA, followed by intracellular staining of κ/λ. CS1 and BCMA expression were analyzed on gated dominant κ light chain. (B) Percentages of CS1 and BCMA positive cells in the dominant clones of AL amyloidosis are presented (N=14). (C) Percentages of CS1 and BCMA positive cells in the dominant clones of multiple myeloma are presented (N=10).

FIG. 1 is a schematic depiction of CS1 CAR (CS1scFv-IgG4(HL-CH3)-CD28gg-Zeta(CO)-T2A-EGFRt_epHIV7), a lentiviral vector containing the CAR construct composed of CS1 scFv, IgG4 hinge region, linker, a CD28 costimulatory domain and CD3ζ Signaling domain. The CAR construct is followed by a T2A ribosomal skip sequence, and then suicide gene EGFRt coding sequence. The CAR and EGFRt molecules are expressed from a single transcript. TABLE 5 presents position of various elements of the vector.

TABLE 5

Functional elements of a CAR_epHIV7

| Regulatory Elements and Genes | Location (Nucleotide Numbers) | Comments |
| --- | --- | --- |
| U5 | 87-171 | 5' Unique sequence |
| psi | 233-345 | Packaging signal |
| RRE | 957-1289 | Rev-responsive element |
| flap | 1290-1466 | Contains polypurine track sequence and central termination sequence to facilitate nuclear import of pre-integration complex |
| EF1p Promoter | 1524-2067 | EF1-alpha Eukaryotic Promoter sequence driving expression of CD19Rop |
|  | 2084-4963 | Therapeutic insert |
| WPRE | 5011-5611 | Woodchuck hepatitis virus derived regulatory element to enhance viral RNA transportation |
| delU3 | 5626-5730 | 3' U3 with deletion to generate SIN vector |
| R | 5731-5811 | Repeat sequence within LTR |
| U5 | 5812-5925 | 3' U5 sequence in LTR |
| $Amp^R$ | 6761-7619 | Ampicillin-resistance gene |
| CoE1 ori | 7682-8563 | Replication origin of plasmid |
| SV40 ori | 8860-=9059 | Replication origin of SV40 |
| CMV promoter | 9073-9672 | CMV promoter to generate viral genome RNA |
| R | 9728-86 | Repeat sequence within LTR | regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

The CMV promoter was replaced by the EF1α-HTLV promoter (EF1p), and the new plasmid was named epHIV7. The EF1p has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been Example 5: Production of Vectors for Transduction of Patient T Cells For each plasmid (CS1 CAR_epHIV7; pCgp; pCMV-G; and pCMV-Rev2), a seed bank is generated, which is used to inoculate the fermenter to produce sufficient quantities of plasmid DNA. The plasmid DNA is tested for identity, sterility and endotoxin prior to its use in producing lentiviral vector.

Briefly, cells are expanded from the 293T working cell (WCB), which has been tested to confirm sterility and the absence of viral contamination. A vial of 293T cells from the 293T WCB is thawed. Cells are grown and expanded until sufficient numbers of cells existed to plate an appropriate number of 10 layer cell factories (CFs) for vector production and cell train maintenance. A single train of cells can be used for production.

The lentiviral vector was produced in sub-batches of up to 10 CFs. Two subbatches can be produced in the same week leading to the production of approximately 20 L of lentiviral supernatant/week. The material produced from all sub-batches were pooled during the downstream processing phase, in order to produce one lot of product. 293T cells were plated in CFs in 293T medium (DMEM with 10% FBS). Factories were placed in a 37° C. incubator and horizontally leveled in order to get an even distribution of the cells on all the layers of the CF. Two days later, cells were transfected with the four lentiviral plasmids described above using the CaPO4 method, which involves a mixture of Tris:EDTA, 2M CaCl2, 2×HBS, and the four DNA plasmids. Day 3 after transfection, the supernatant containing secreted lentiviral vectors was collected, purified and concentrated. After the supernatant was removed from the CFs, End-of-Production Cells were collected from each CF. Cells were trypsinized from each factory and collected by centrifugation. Cells were resuspended in freezing medium and cryopreserved. These cells were later used for replication-competent lentivirus (RCL) testing.

To purify and formulate vectors crude supernatant was clarified by membrane filtration to remove the cell debris. The host cell DNA and residual plasmid DNA were degraded by endonuclease digestion (Benzonase®). The viral supernatant was clarified of cellular debris using a 0.45 µm filter. The clarified supernatant was collected into a pre-weighed container into which the Benzonase® is added (final concentration 50 U/mL). The endonuclease digestion for residual plasmid DNA and host genomic DNA as performed at 37° C. for 6 h. The initial tangential flow ultrafiltration (TFF) concentration of the endonuclease-treated supernatant was used to remove residual low molecular weight components from the crude supernatant, while concentrating the virus ~20 fold. The clarified endonuclease-treated viral supernatant was circulated through a hollow fiber cartridge with a NMWCO of 500 kD at a flow rate designed to maintain the shear rate at ~4,000 sec-1 or less, while maximizing the flux rate. Diafiltration of the nuclease-treated supernatant was initiated during the concentration process to sustain the cartridge performance. An 80% permeate replacement rate was established, using 4% lactose in PBS as the diafiltration buffer. The viral supernatant was brought to the target volume, representing a 20-fold concentration of the crude supernatant, and the diafiltration was continued for 4 additional exchange volumes, with the permeate replacement rate at 100%.

Further concentration of the viral product was accomplished by using a high speed centrifugation technique. Each sub-batch of the lentivirus was pelleted using a Sorvall RC-26 plus centrifuge at 6000 RPM (6,088 RCF) at 6° C. for 16-20 h. The viral pellet from each sub-batch was then reconstituted in a 50 mL volume with 4% lactose in PBS. The reconstituted pellet in this buffer represents the final formulation for the virus preparation. The entire vector concentration process resulted in a 200-fold volume reduction, approximately. Following the completion of all of the sub-batches, the material was then placed at −80° C., while samples from each sub-batch were tested for sterility. Following confirmation of sample sterility, the sub-batches were rapidly thawed at 37° C. with frequent agitation. The material was then pooled and manually aliquoted in the Class II Type A/B3 biosafety cabinet in the viral vector suite. A fill configuration of 1 mL of the concentrated lentivirus in sterile USP class 6, externally threaded O-ring cryovials was used. Center for Applied Technology Development (CATD)'s Quality Systems (QS) at COH released all materials according to the Policies and Standard Operating Procedures for the CBG and in compliance with current Good Manufacturing Practices (cGMPs).

To ensure the purity of the lentiviral vector preparation, it is tested for residual host DNA contaminants, and the transfer of residual host and plasmid DNA. Among other tests, vector identity is evaluated by RT-PCR to ensure that the correct vector is present. All release criteria are met for the vector intended for use in this study.

Example 6: Preparation of $T_{CM}$ Cells Suitable for Expression of CS-1 CAR

T lymphocytes are obtained from a patient by leukopheresis, and the appropriate allogenic or autologous T cell subset, for example, Central Memory T cells ($T_{CM}$), are genetically altered to express the CAR, then administered to the patient by any clinically acceptable means, to achieve anti-cancer therapy.

$T_{CM}$ that are CD8+ are isolated essentially as described in Wang et al. (*J Immunology* 35:689, 2012). Briefly, on the day of leukapheresis, PBMC were isolated by density gradient centrifugation over Ficoll-Paque followed by two washes in PBS/EDTA. PBMC were then washed once in PBS, resuspended in X Vivo15 media containing 10% fetal calf serum (FCS), transferred to a 300 cc transfer bag, and stored on a 3-D rotator overnight at room temperature (RT). The following day, up to $5 \times 10^9$ PBMC were incubated in a 300 cc transfer bag with clinical grade anti-CD4 (2.5 mL), anti-CD14 (1.25 mL), and anti-CD45RA (2.5 mL) microbeads (Miltenyi Biotec) for 30 minutes at RT in X Vivo15 containing 10% FCS. CD4+, CD14+ and CD45RA+ cells were then immediately depleted using the CliniMACS™ depletion mode according to the manufacturer's instructions (Miltenyi Biotec). After centrifugation, the unlabeled negative fraction of cells was resuspended in CliniMACS™ PBS/EDTA buffer (Miltenyi Biotec) containing 0.5% human serum albumin (HSA) and then labeled with clinical grade biotinylated-DREG56 mAb (COHNMC CBG) at 0.1 mg/106 cells for 30 minutes at RT. The cells were then washed and resuspended in a final volume of 100 mL CliniMACS™ PBS/EDTA containing 0.5% HSA and transferred into a new 300 cc transfer bag. After a 30 minute incubation with 1.25 mL anti-biotin microbeads (Miltenyi Biotec), the CD62L+ fraction of PBMC (CD8+ $T_{CM}$) was purified with positive selection on CliniMACS™ according to the manufacturer's instructions, and resuspended in X Vivo15 containing 10% FCS.

$T_{CM}$ that are CD8+/CD4+ are prepared using a modification of the forgoing process by modifying the CD4+, CD14+ and CD45RA+ selection to a CD14+ and CD45RA+ selection. The method uses a two-step process on the CliniMACS™ device to first deplete CD14+ and CD45RA+ cells, then to positively select CD62L+ cells. This modified platform generates $50 \times 10^6$ bulk $T_{CM}$ from a single leukopheresis.

Following enrichment, $T_{CM}$ cells are formulated in complete X-Vivo15 plus 50 IU/mL IL-2 and 0.5 ng/mL IL-15 and transferred to a Teflon cell culture bag, where they are stimulated with Dynal ClinEx™ Vivo CD3/CD28 beads. Up to five days after stimulation, cells are transduced with lentiviral vector encoding CS1 CAR at a multiplicity of infection (MOI) of about 3. Cultures are maintained for up to 42 days with addition of complete X-Vivo15 and IL-2 and IL-15 cytokine as required for cell expansion (keeping cell density between $3 \times 10^5$ and $2 \times 10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium.

On the day(s) of T cell infusion, the cryopreserved and released product will be thawed, washed and formulated for re-infusion. The cryopreserved vials containing the released cell product will be removed from liquid nitrogen storage, thawed, cooled and washed with a PBS/2% human serum albumin (HSA) Wash Buffer. After centrifugation, the supernatant will be removed and the cells resuspended in a Preservative-Free Normal Saline (PFNS)/2% HSA infusion diluent. Samples will be removed for quality control testing.

Example 7: Amino acid Sequence of CS1 CAR (CS1scFv-IgG4(HL-CH3)-CD28tm-CD28gg-Zeta-T2A-EGFRt)

The complete amino acid sequence of CS1scFv-IgG4 (HL-CH3)-CD28tm-CD28gg-Zeta-T2A-EGFRt is depicted in FIG. 4. The entire sequence (SEQ ID NO:29) includes: a 22 amino acid GMCSF signal peptide (SEQ ID NO:26), a CS1 scFv sequence (SEQ ID NO:1); a IgG4 hinge sequence (SEQ ID NO:3; with amino acid substitutions S to P shaded); a 10 amino acid linker (SEQ ID NO:2); IgG4 CH3 sequence (SEQ ID NO:12); a 28 amino acid CD28 transmembrane domain sequence (SEQ ID NO:14); a CD28gg co-stimulatory domain sequence (SEQ ID NO:23; LL to GG amino acid changes highlighted); a 3 amino acid Gly linker; a 112 amino acid CD3ζ sequence (SEQ ID NO:21); a 24 amino acid T2A skip sequence (SEQ ID NO:27); and EGFRt sequence (SEQ ID NO:28).

What is claimed is:

1. A method for treating light chain amyloidosis comprising administering to a patient in need thereof a population of human T cells expressing a chimeric antigen receptor, wherein chimeric antigen receptor comprises an amino acid sequence selected from: SEQ ID NOs: 30, 31, 33, 34, 36, 37, 39, 40, 42, 43, 45, and 46.

2. The method of claim 1, wherein the chimeric antigen receptor consists of an amino acid sequence identical to an amino acid sequence selected from: SEQ ID NOs: 30, 31, 33, 34, 36, 37, 39, 40, 42, 43, 45, and 46.

3. The method of claim 1, wherein at least 20%, 30%, or 40% of the transduced human T cells are central memory T cells.

4. The method of claim 1, wherein at least 30% of the transduced human T cells are CD4+ and CD62L+ or CD8+ and CD62L+.

5. The method of claim 1, wherein the population of human T cells are autologous to the patient.

6. The method of claim 1, wherein the population of human T cells are allogenic to the patient.

7. A method for treating light chain amyloidosis comprising administering to a patient in need thereof a population of human T cells expressing transduced by a vector comprising an expression cassette encoding a chimeric antigen receptor, wherein chimeric antigen receptor comprises:
(a) a CS1 scFv comprising SEQ ID NO: 1; a spacer domain comprising SEQ ID NO: 9; a transmembrane domain comprising SEQ ID NO: 15; a co-signaling domain comprising SEQ ID NO: 23; and a CD3 ζ signaling domain comprising SEQ ID NO: 21;
(b) a CS1 scFv comprising SEQ ID NO: 1; a spacer domain comprising SEQ ID NO: 9; a transmembrane domain comprising SEQ ID NO: 16; a co-signaling domain comprising SEQ ID NO: 24; and a CD3 ζ signaling domain comprising SEQ ID NO: 21;
(c) a CS1 scFv comprising SEQ ID NO: 1; a spacer domain comprising SEQ ID NO: 11; a transmembrane domain comprising SEQ ID NO: 16; a co-signaling domain comprising SEQ ID NO: 24; and a CD3 ζ signaling domain comprising SEQ ID NO: 21;
(d) a CS1 scFv comprising SEQ ID NO: 1; a spacer domain comprising SEQ ID NO: 11; a transmembrane domain comprising SEQ ID NO: 15; a co-signaling domain comprising SEQ ID NO: 23; and a CD3 ζ signaling domain comprising SEQ ID NO: 21;
(e) a CS1 scFv comprising SEQ ID NO: 1; a spacer domain comprising SEQ ID NO: 2; a transmembrane domain comprising SEQ ID NO: 16; a co-signaling domain comprising SEQ ID NO: 24; and a CD3 ζ signaling domain comprising SEQ ID NO: 21; and
(f) a CS1 scFv comprising SEQ ID NO: 1; a spacer domain comprising SEQ ID NO: 2; a transmembrane domain comprising SEQ ID NO: 15; a co-signaling domain comprising SEQ ID NO: 23; and a CD3 ζ signaling domain comprising SEQ ID NO: 21.

8. The method of claim 7, wherein the chimeric antigen receptor comprises an amino acid sequence selected from any one of SEQ ID NOs: 30, 31, 33, 34, 36, 37, 39, 40, 42, 43, 45, and 46.

9. The method of claim 7, wherein at least 30% of the transduced human T cells are CD4+ and CD62L+ or CD8+ and CD62L+.

10. The method of claim 7, wherein the population of human T cells are autologous to the patient.

11. The method of claim 7, wherein the population of human T cells are allogenic to the patient.

* * * * *